United States Patent
Vaishya et al.

(10) Patent No.: US 11,446,128 B2
(45) Date of Patent: Sep. 20, 2022

(54) SLING AND METHOD OF FORMING SAME

(71) Applicant: Caldera Medical, Inc., Agoura Hills, CA (US)

(72) Inventors: Manish Vaishya, Agoura Hills, CA (US); Ryan Neimy, Agoura Hills, CA (US)

(73) Assignee: Caldera Medical, Inc., Agoura Hills, CA (US)

(*) Notice: Subject to any disclaimer, the term of this patent is extended or adjusted under 35 U.S.C. 154(b) by 329 days.

(21) Appl. No.: 16/565,378

(22) Filed: Sep. 9, 2019

(65) Prior Publication Data

US 2020/0078155 A1    Mar. 12, 2020

Related U.S. Application Data

(60) Provisional application No. 62/728,714, filed on Sep. 7, 2018.

(51) Int. Cl.
 *A61F 2/00*  (2006.01)
 *B29C 51/26*  (2006.01)
 *B29L 31/00*  (2006.01)

(52) U.S. Cl.
 CPC .......... *A61F 2/0045* (2013.01); *B29C 51/266* (2013.01); *A61F 2210/0071* (2013.01); *A61F 2220/0008* (2013.01); *A61F 2230/0067* (2013.01); *A61F 2240/001* (2013.01); *B29L 2031/7532* (2013.01)

(58) Field of Classification Search
 CPC ........ A61F 2/00; A61F 2/0004; A61F 2/0031; A61F 2/0036; A61F 2/004; A61F 2/0045; A61F 2/0063; A61F 2210/0071; A61F 2220/0008; A61F 2230/0067; A61F 2240/001; B29C 51/08; B29C 51/082; B29C 51/20; B29C 51/266; B29C 51/267
 See application file for complete search history.

(56) References Cited

U.S. PATENT DOCUMENTS

| | | |
|---|---|---|
| 2005/0177022 A1 | 8/2005 | Chu et al. |
| 2006/0195007 A1 | 8/2006 | Anderson et al. |
| 2008/0287731 A1 | 11/2008 | Kuntz |
| 2009/0221867 A1 | 9/2009 | Ogdah et al. |
| 2010/0105979 A1* | 4/2010 | Hamel ............. A61B 17/06109 600/30 |
| 2010/0256442 A1 | 10/2010 | Ogdah et al. |
| 2013/0324789 A1* | 12/2013 | Smith ................... A61F 2/0045 600/30 |

OTHER PUBLICATIONS

WIPO, U.S. International Search Authority, International Search Report and Written Opinion dated Nov. 4, 2019 in International Patent Application No. PCT/US2019/050092, 8 pages.

* cited by examiner

*Primary Examiner* — Carrie R Dorna
(74) *Attorney, Agent, or Firm* — Inskeep IP Group, Inc.

(57) ABSTRACT

A medical sling for supporting an anatomical feature having ends that are tapered using a folding fixture and then thermoset. The thermoset ends hold the bunched or folded shape thus allowing the ends to be removed from the fixture and placed into a mold assembly where anchors are molded over the ends.

21 Claims, 20 Drawing Sheets

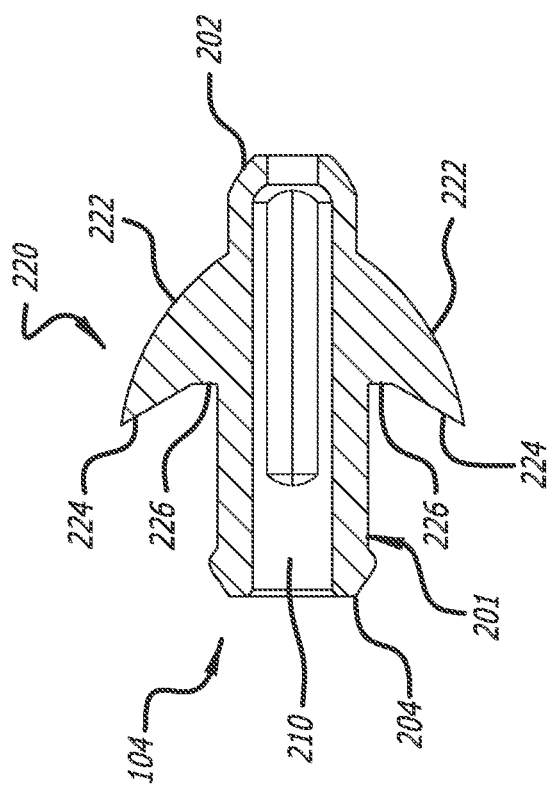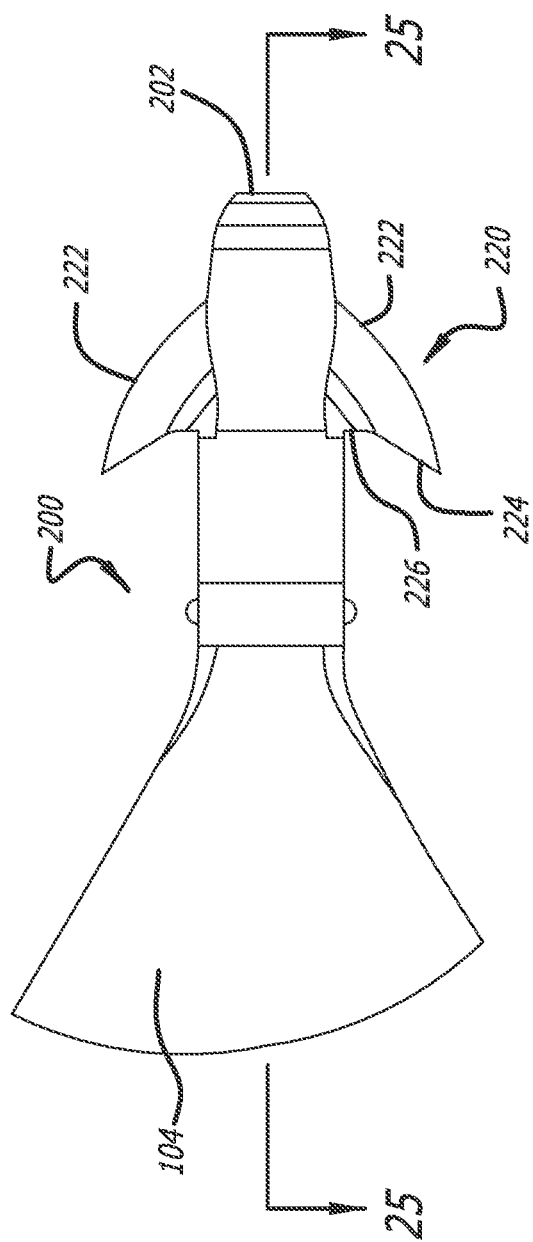

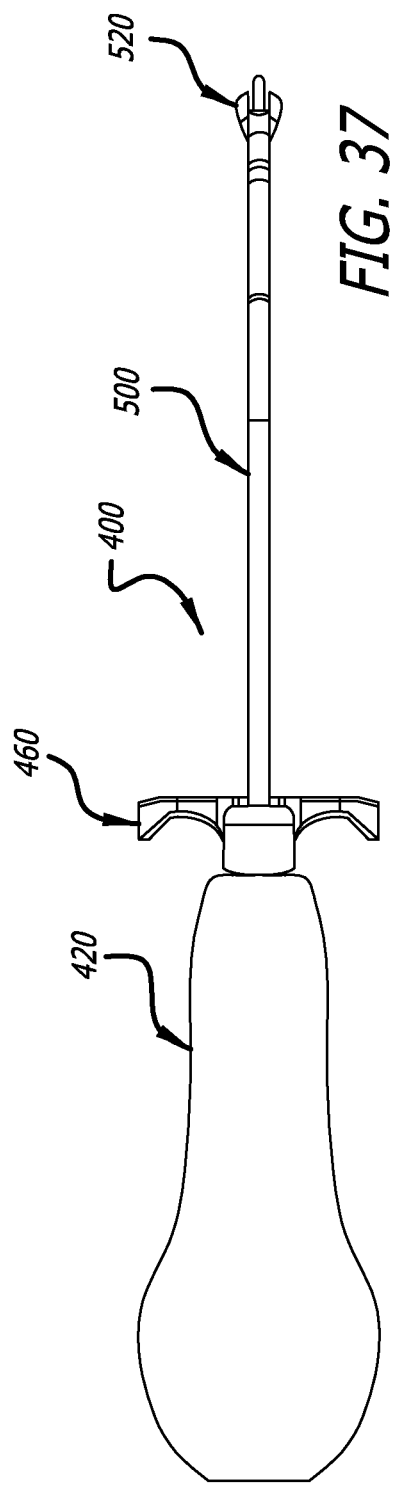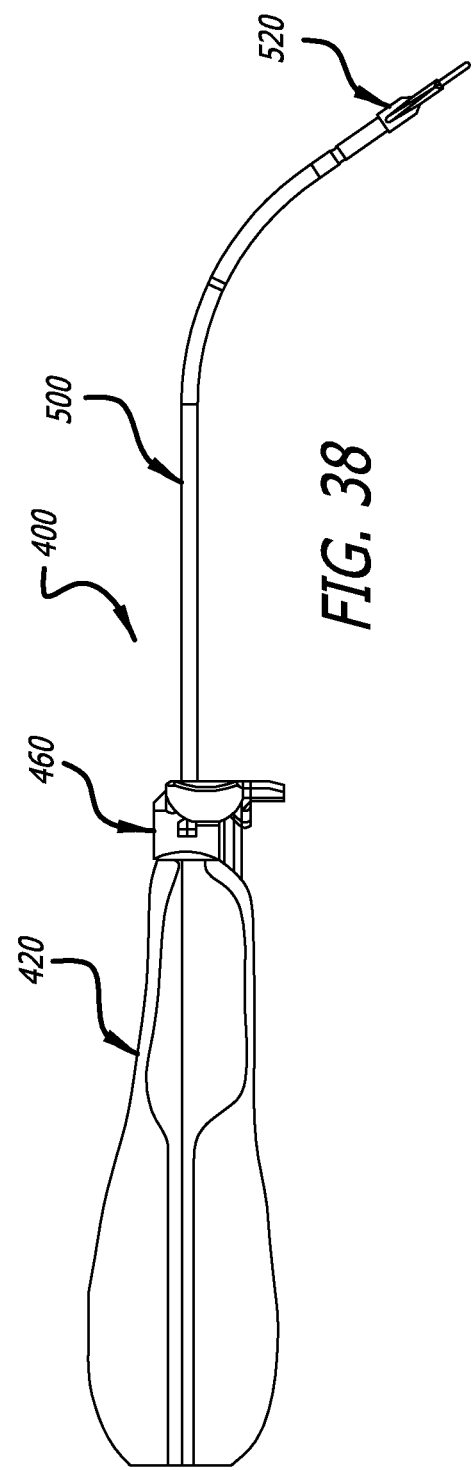

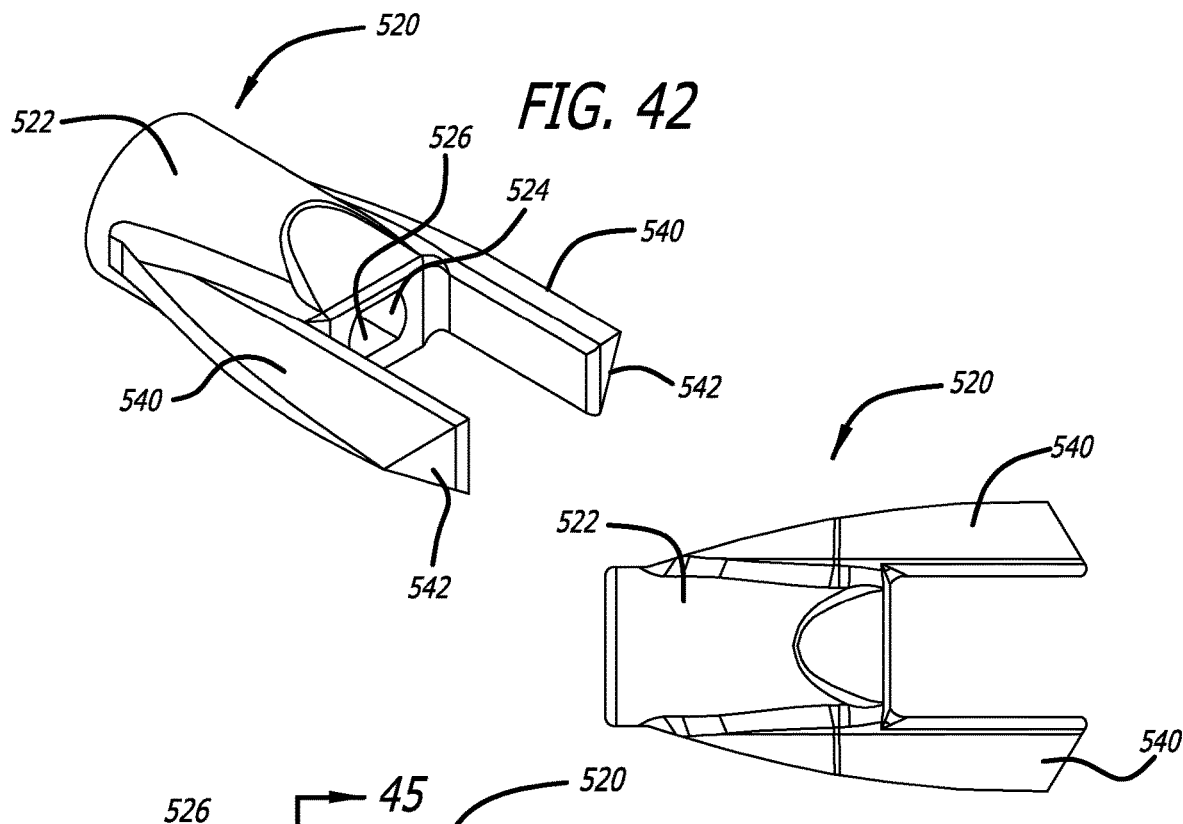
FIG. 42
FIG. 43
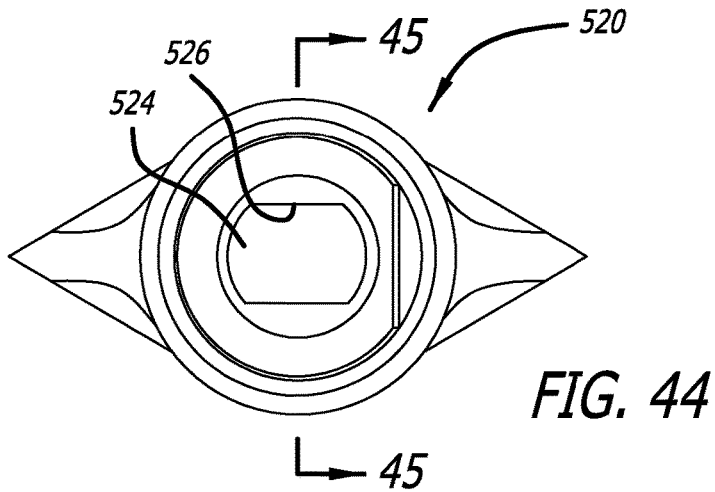
FIG. 44
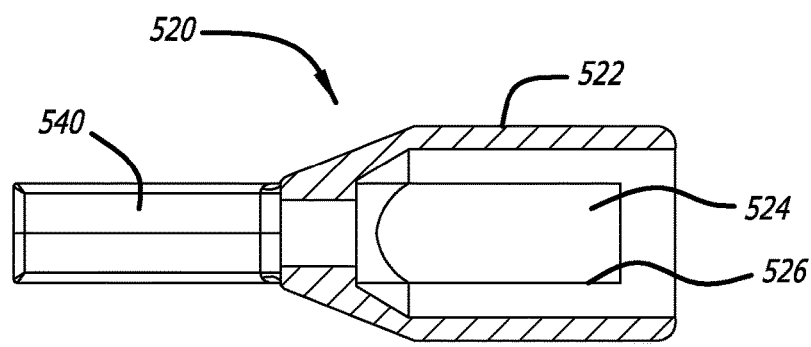
FIG. 45

SLING AND METHOD OF FORMING SAME

RELATED APPLICATIONS

This application claims priority to U.S. Provisional Application Ser. No. 62/728,714 filed Sep. 7, 2018 entitled Sling and Method of Forming Same, which is hereby incorporated herein by reference in its entirety.

FIELD OF THE INVENTION

The present invention pertains to the field of medical devices for anchoring and supporting anatomical structure, such as the urethra, with implantable slings that are operative to provide support for such structure. More particularly, the present invention relates to a single incision sling (SIS) employed for stress incontinence of patients.

BACKGROUND OF THE INVENTION

Single incision slings employed for stress incontinence patients typically incorporate polymeric anchors on each side that clutch the tissue for retention. Due to the small size of the anchors, the mesh needs to be reduced in size at the ends or interface of the mesh with the anchor. Previous methods result in either reduced strength of the sling assembly, higher tissue erosion during implantation, or abrupt profile changes causing tissue trauma. Currently used methods achieve this reduction in size by tapering down the mesh using a suture filament or by simply increasing the size of the anchor. However, these methods result in reduced strength of the sling assembly, higher tissue erosion during implantation, and/or abrupt profile changes in the mesh prone to causing tissue trauma. Accordingly, there is a substantial need in the art for a urethral sling assembly for the treatment of incontinence that provides higher strength, lower tissue erosion during implantation and avoids abrupt profile changes causing tissue trauma.

SUMMARY OF THE INVENTION

The present invention provides a sling assembly without compromising the strength of the sling assembly or increasing the size of the anchors that clasp the tissue for retention. The present invention discloses a unique method of affixing the relatively larger widths of the proximal and the distal ends of the sling mesh within the much smaller diameters or profiles of anchors without trimming the mesh of the sling. This method of affixing the sling ends inside the anchors is achieved through a process of overmolding. In some embodiments, the widths of the proximal and the distal ends of the sling mesh are about 11 mm and are secured inside the anchors at both ends where the anchors have diameters of about 2 mm.

The present invention provides a unique design of sling assembly where both ends of the sling mesh with higher widths are secured within much smaller diameters of anchors without cutting the sling mesh at both ends or increasing the size of the anchors. Thus, the sling assembly retains its strength and reduces the risk of tissue erosion and tissue trauma.

In some embodiments, the anchors and the sling are made of a polymeric thermoplastic material such as polyethylene and/or polypropylene.

The method of thermosetting and molding the mesh within the plastic anchor is unique and inventive because there are no changes to the cross-sectional material of the mesh, thus preserving the mesh strength and not requiring the trimming of mesh, allowing preservation of thermally-treated edges of the mesh. Furthermore, the resulting funnel shape and smooth transition of mesh allows easier implantation with minimum tissue trauma and allows a miniature anchor to minimize tissue trauma. Also, due to retaining of all the sling filaments, the bond strength is maximized between mesh and the anchor.

One aspect of the invention provides a method of forming a medical sling device that includes providing a rectangular strip of material having a two end portions and an elongate body between the two end portions. At least one of said two end portions is then tapered without removing material therefrom by bunching the material in such a manner that a terminus of the end portion has a smaller width than an intersection between the end portion and the elongate body. Next the end or ends are thermoset such that the end or ends maintains the smaller width when unconstrained. The thermosetting process may also create a crescent shape in the end. Next the end portion is placed in a mold and an anchor is formed around the terminus of the end portion.

In one aspect the bunching of the material results in a waveform. The waveform may take the form of an "m" or a "w" and may have smooth curves forming the "m" or "w".

The bunching of the material may be accomplished by pulling the rectangular strip through a fixture assembly. The fixture assembly may include a fixture bottom having a groove with a wide end and a narrow end, the narrow end having a curved form with gaps on either side of said curved form. The fixture assembly may also include a fixture top having a groove with a wide end and a narrow end, the narrow end having a center fin and a curved form on either side of the center fin. When the fixture top is placed on the fixture bottom and aligned therewith, the center fin may point down toward the fixture bottom curved form, thereby creating a wave-like gap through which the rectangular strip may be pulled to create the smaller width in said at least one end portion. The wave-like gap may take the form of an "m" or a "w" and may have smooth curves forming the "m" or "w".

In another aspect, the fixture includes a shaping rod extending from said narrow end of said groove. In this aspect thermosetting the end or ends involves pulling the rectangular strip through the fixture assembly to create the waveform and further onto a shaping rod. Heat shrink tubing is then heat-shrunk over the waveform to form the waveform into the shaping rod to create a crescent-shape. The tubing may then be removed prior to removing the end from the fixture and placing it into the mold to create the anchors.

Another aspect of the invention provides a method of forming a medical sling device that involves providing a rectangular strip of material having a two end portions and an elongate body between the two end portions, then tapering at least one of the two end portions without removing the material therefrom by creating a wave-like configuration in the material such that a terminus of the at least one end portion has a smaller width than an intersection between the at least one end portion and the elongate body; placing the at least one end portion in a mold and forming an anchor around the terminus.

In one aspect this method further includes thermosetting the at least one end such that the wave-like configuration is maintained while placing the at least one end portion in the mold.

In another aspect bunching the material involves pulling the strip through a fixture assembly.

In yet another aspect the fixture assembly includes a fixture bottom having a groove with a wide end and a narrow end, the narrow end having a curved form with gaps on either side of the curved form; and a fixture top having a groove with a wide end and a narrow end, the narrow end having a center fin and a curved form on either side of the center fin. When the fixture top is placed on the fixture bottom and aligned therewith, the center fin points down toward the fixture bottom curved form, thereby creating a wave-like gap through which the strip may be pulled to create the wave-like configuration in the at least one end portion.

Yet another aspect of the invention provides a medical sling that includes an elongate strip of material having two ends and a support portion between the two ends wherein each of the two ends is formed into a wave-like pattern and subsequently thermoset into a crescent or semicircle and has anchors over-molded around each of the two ends.

In one aspect the anchors of the medical sling each have a body and tissue-grabbing features extending outwardly from the body. The tissue grabbing features may include at least one wing having a leading edge and a trailing edge and wherein the leading edge sweeps from the body back to the trailing edge. The trailing edge may extend forward from the leading edge to a lateral edge. The lateral edge may extend perpendicularly from the body to the trailing edge.

In another aspect the elongate strip of material has a rectangular shape prior to the two ends being formed into a wave-like pattern.

In yet another aspect the wave-like pattern creates a taper in the elongate strip near each of the two ends.

In still another aspect the anchors each further include a cavity useable to receive an implantation device.

In another aspect the wave-like pattern is thermoset into a crescent shape that partially surrounds the cavity.

BRIEF DESCRIPTION OF FIGURES

FIG. 23 is a section view of the embodiment of the anchor of FIG. 22 taken along section lines D-D;

FIG. 24 is a plan view of an embodiment of an anchor of the invention;

FIG. 37 is a plan view of an embodiment of an introducer of the invention;

FIG. 38 is a side elevation of an embodiment of an introducer of the invention;

FIG. 42 is a perspective view of an embodiment of an end piece of the invention;

FIG. 43 is a plan view of an embodiment of an end piece of the invention;

FIG. 44 is a back elevation of an embodiment of an end piece of the invention;

FIG. 45 is a sectional view of the embodiment of the end piece of FIG. 44 taken along lines B-B;

DESCRIPTION OF EMBODIMENTS

Figure 1:
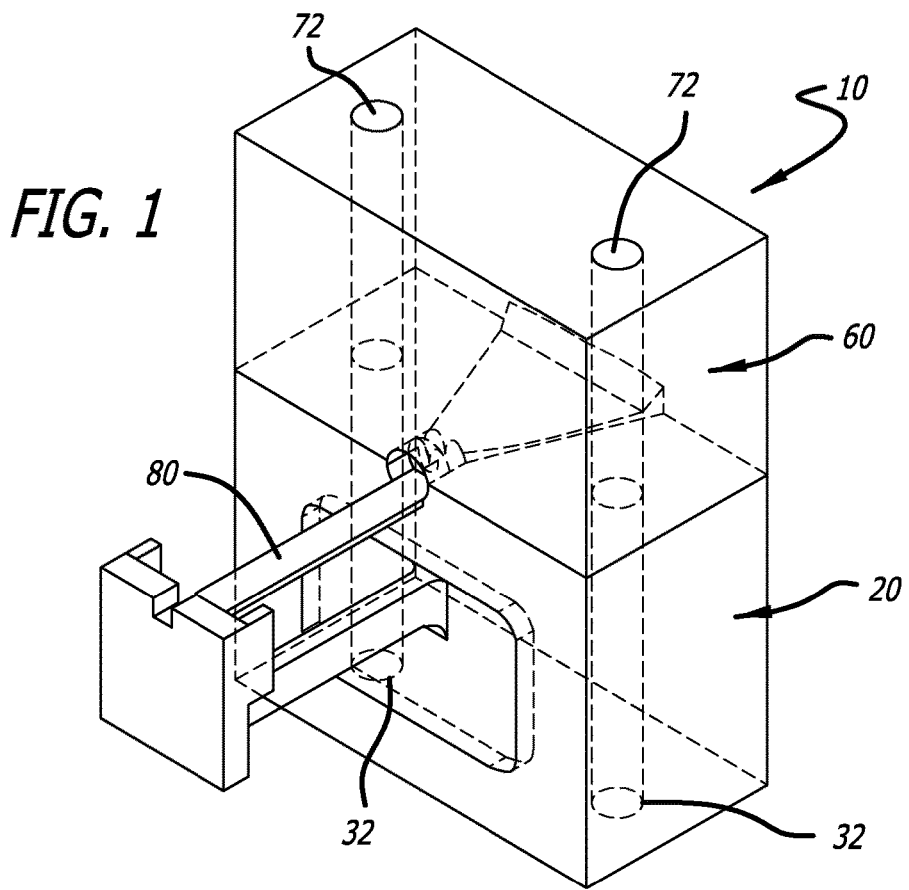
FIG. 1 is a transparent perspective view of an embodiment of a fixture of the invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

In the present application, the sling is designed in such a way that the mesh is reduced in width, rolled, folded, and/or bunched into a small cross-section that can be contained within the plastic anchor. The method of reducing the width of the mesh is done with a fixture assembly that allows smooth transition with a simple pulling of the mesh. Subsequently, the mesh is thermally treated to retain the small cross-sectional shape prior to over-molding inside the anchor.

Figure 2:
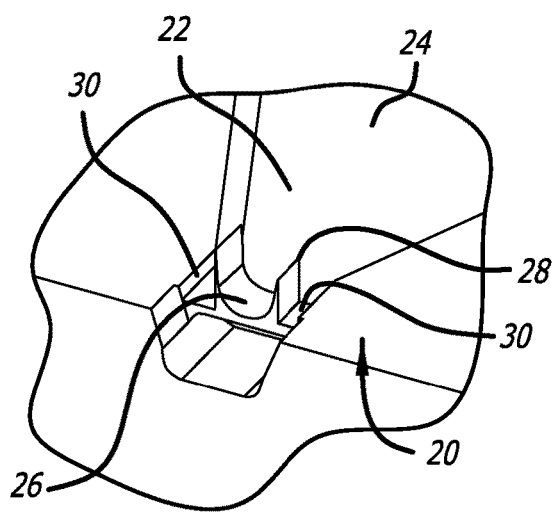
FIG. 2 is a partial perspective view of an embodiment of a bottom portion of a fixture of the invention.

FIG. 1 describes a fixture assembly 10 which is used for rolling the sling mesh into a smaller cross-sectional profile. The fixture assembly comprises two major parts, including, a fixture bottom 20 and a fixture top 60. FIG. 2 demonstrates the fixture bottom part 20 and FIG. 3 demonstrates the fixture top part 60. Each of the fixture bottom 20 and the fixture top 60 define grooves 22 and 62, respectively, and the grooves 22, 62 of the fixture bottom and fixture top taper into a smaller cross-sectional area at the terminal ends forming a semicircular pattern. As seen in FIGS. 2 and 4, the groove 22 tapers from a wide end 24 to a narrow end 26. The narrow end 26 includes a crescent-shaped, semi-circular or curved form 28 that includes gaps 30 on either side, the function of which will be explained below.

Figure 3:
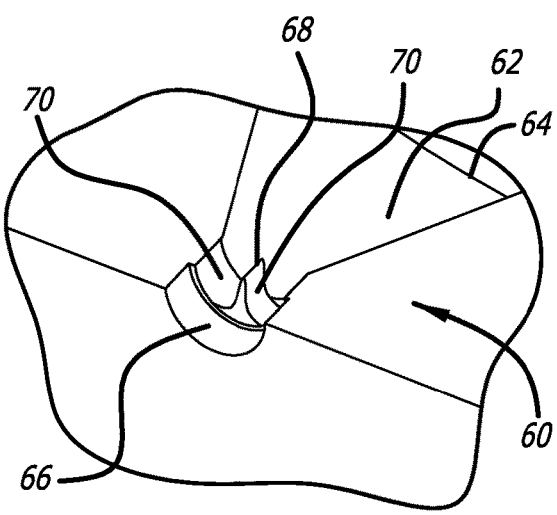
FIG. 3 is a partial perspective view of an embodiment of a top portion of a fixture of the invention.
Figure 4:
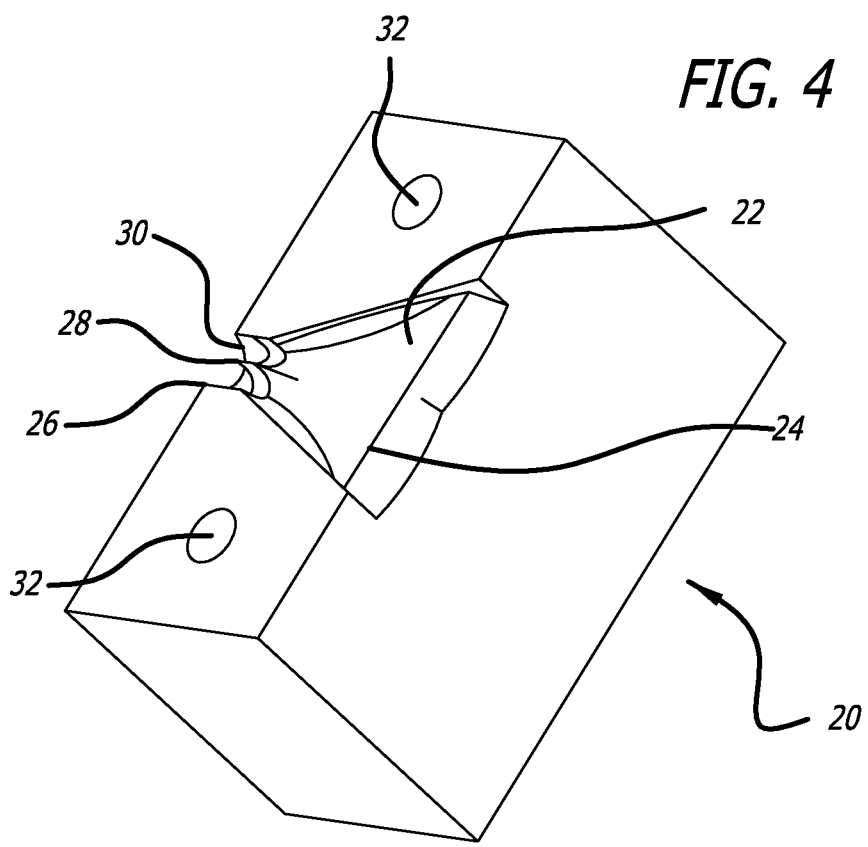
FIG. 4 is a perspective view of an embodiment of a bottom portion of a fixture of the invention.
Figure 5:
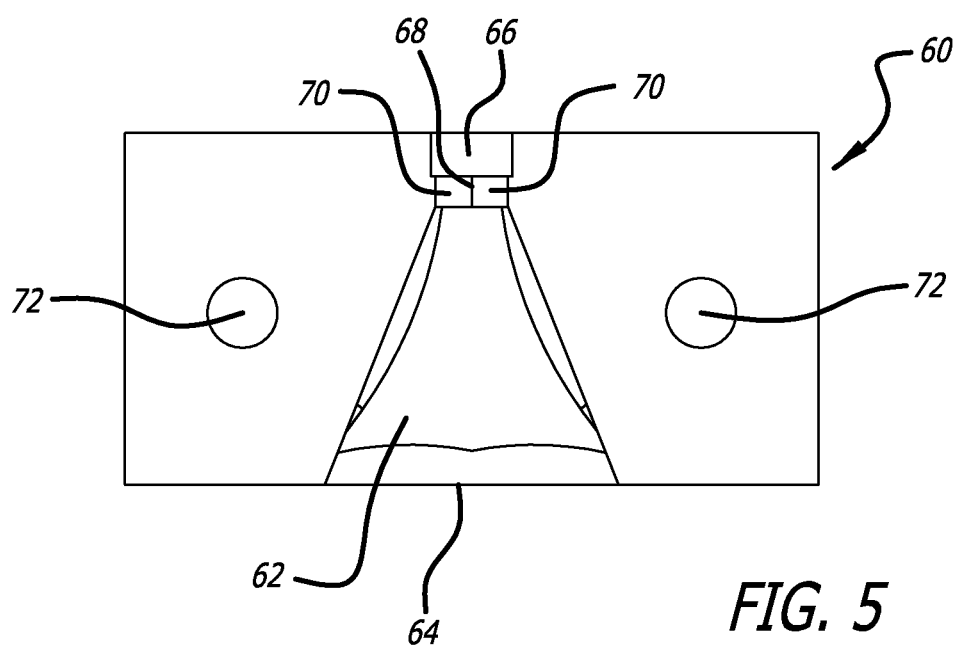
FIG. 5 is a perspective view of an embodiment of a top portion of a fixture of the invention.

FIGS. 3 and 5 show the detail of the groove 62 of the fixture top 60. The groove 62 also tapers from a wide end 64 to a narrow end 66. The narrow end 66 includes a center fin 68 that results in two curved forms 70, one on either side of the fin 68.

Figure 6:
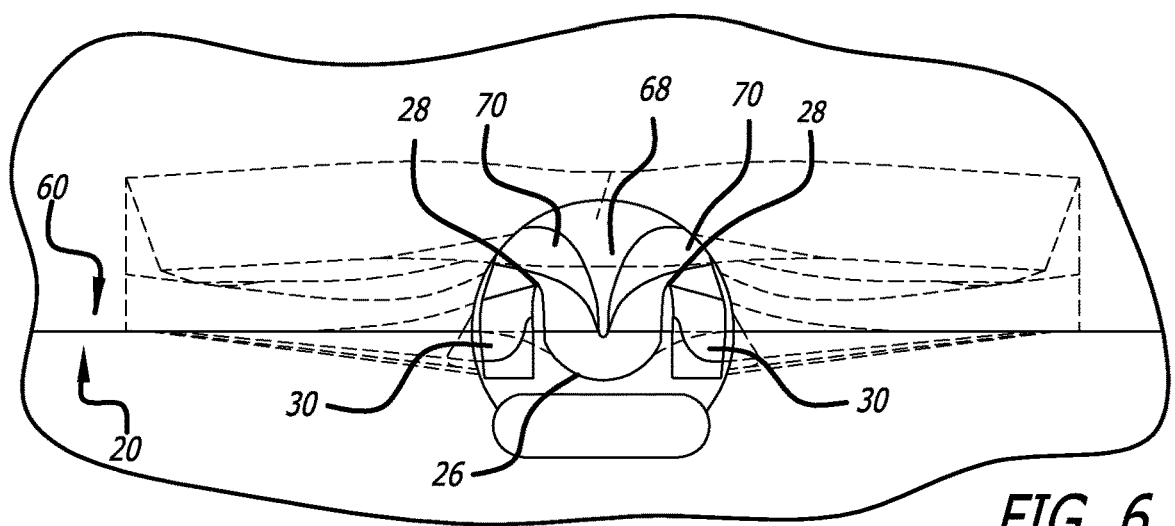
FIG. 6 is a partial front elevation of an embodiment of a fixture of the invention.
Figure 7:
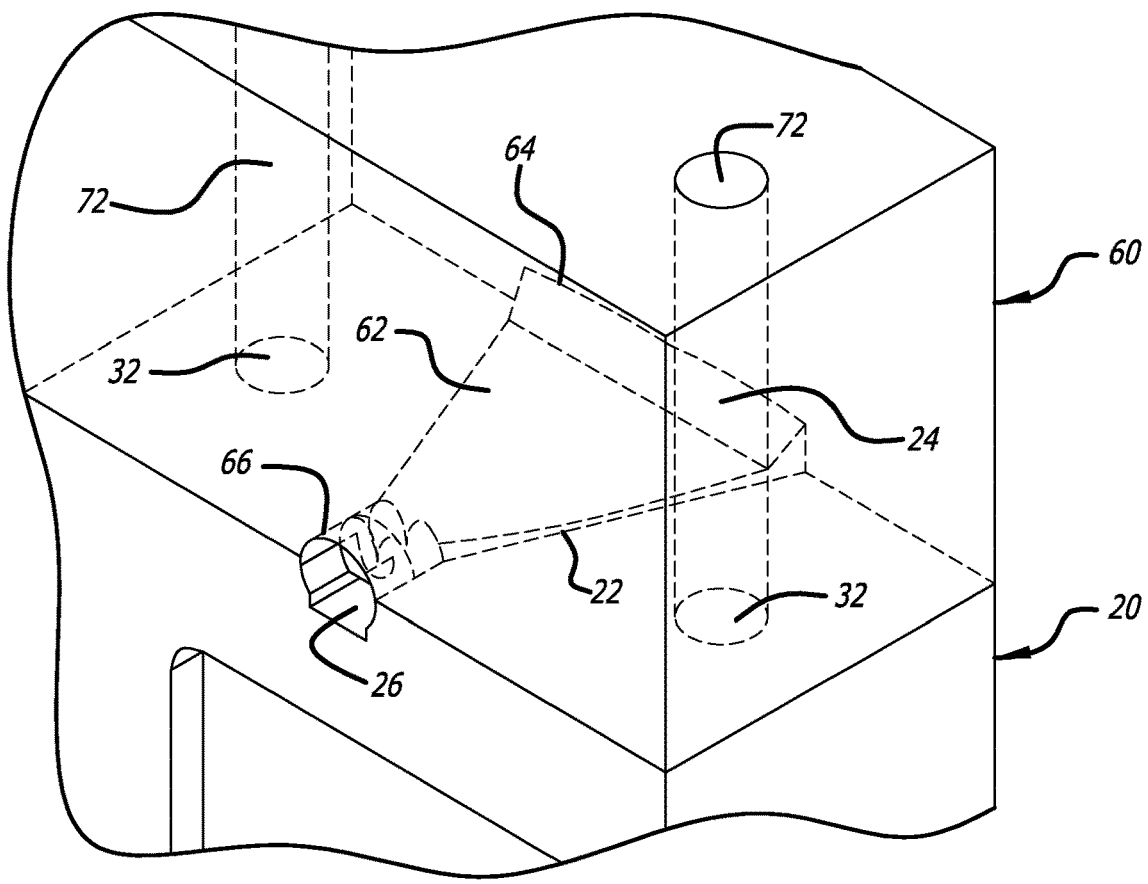
FIG. 7 is a partial perspective view of an embodiment of a fixture of the invention in which the top is depicted as transparent to show internal detail.

As seen in FIGS. 6 and 7, when assembled, the fixture bottom and fixture top align with each other such that the tapered ends 26 and 66 of mating grooves 22 and 62 form a tapered circular end. FIG. 6 demonstrates a front view of this tapered circular end of the fixture assembly in an assembled state. FIG. 7 is another view of the fixture assembly in an assembled state showing holes 32 (bottom) and 72 (top) through which locking pins are employed or inserted to keep the fixture bottom and fixture top securely connected and to prevent accidental disengagement. The sling mesh is pulled through this groove of tapered circular end.

Hereafter, the applicant discloses the method of securing mesh within the plastic anchors at both ends to form the Single Incision Sling. The method involves three steps.

Figure 8A:
FIGS. 8a-8g depict a sequence of end views of configurations of a mesh strip being pulled through an embodiment of a fixture of the invention.
Figure 8B:
Figure 8C:
Figure 8D:
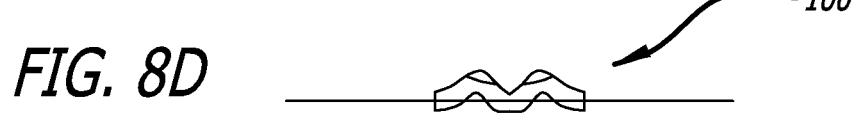
Figure 8E:
Figure 8F:
Figure 8G:
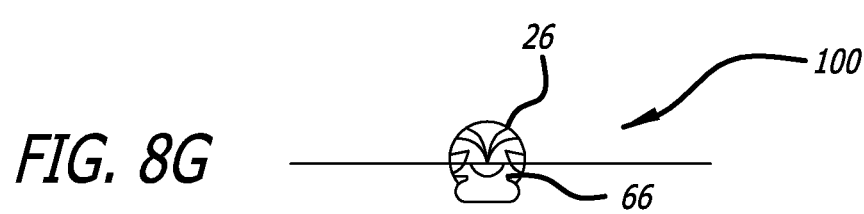

The first step is forming the sling 100. FIGS. 8a-g demonstrate how the reduced width form of the sling mesh is formed. For clarity, only the resulting shape of the sling 100 is shown at various points as it is pulled through the mated grooves 22 and 62. FIG. 8a thus represents the shape of the sling 100 near the wide ends 24 and 64. FIGS. 8b-8f show the gradual progression in the wave-like M-shape formed in the sling as it is pulled toward and, in FIG. 8g, through the narrow ends 26 and 66. In FIG. 8a, the sling mesh is manipulated into a smaller cross-section by gently pulling one end of a mesh through the tapered circular end of the fixture assembly. The M-shape results in a smaller cross-sectional area and is created by the configuration of the forms 28 and 70, the fin 68, and the gaps 30.

Figure 9A:
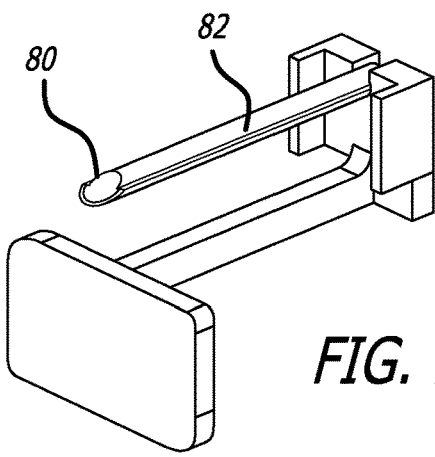
FIG. 9a is a right-side perspective view of an embodiment of a shaping rod of the invention.
Figure 9B:
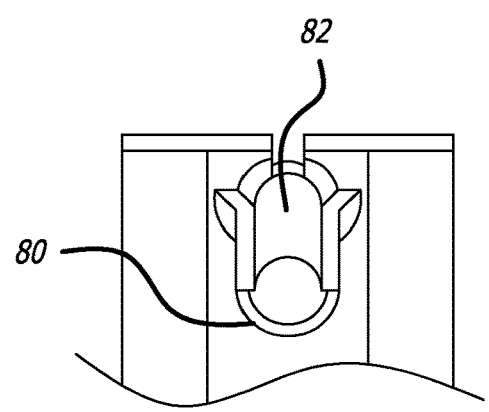
FIG. 9b is a perspective view of an embodiment of a shaping rod of the invention.
Figure 9C:
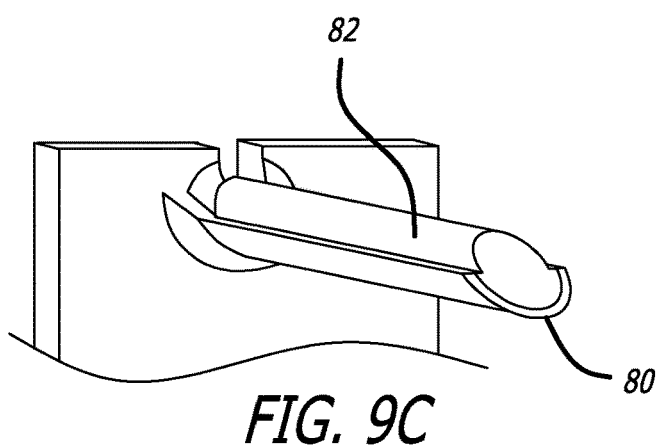
FIG. 9c is a left-side perspective view of an embodiment of a shaping rod of the invention.

The second step is thermally forming or setting the wave-like M-shaped end of the mesh. In this step, the wave-like M-shaped smaller cross-sectional end of the sling 100 is pulled through a portion of heat shrink tube 82 and over a shaping rod 80. FIGS. 1 and 9 show a shaping rod 80 which is protruded from the fixture assembly. The M-shaped smaller cross-sectional end of the sling, within the shrink tube, is wrapped around the shaping rod, and the M-shaped end is exposed to thermosetting conditions to form a C-shaped end thermoformed mesh end. The thermoset mesh end is cooled, the shaping rod 80 is withdrawn, the shrink tube 82 removed, and the shaped mesh end 102 is trimmed to the desired length, shown in FIG. 10.

Figure 10:
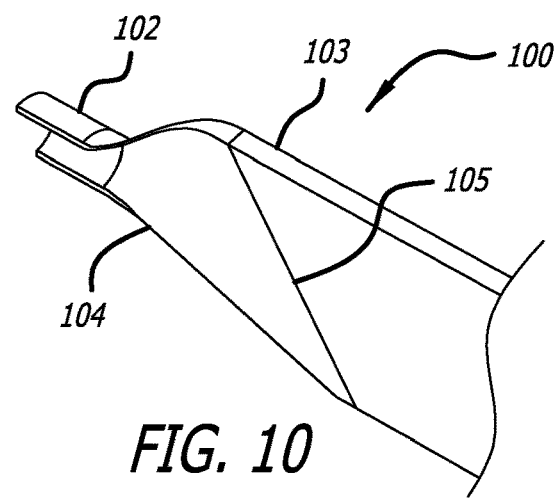
FIG. 10 is a perspective view of one end of an embodiment of a sling of the invention.

FIG. 10 shows a sling 100 having mesh body 103 which has undergone the second step, resulting in thermosetting to form a crescent-shaped terminal end or terminus 102. The mesh of the sling is made of, for example, polyethylene or polypropylene and after exposing to the elevated temperature of the thermosetting condition the mesh is reshaped to a thermoset form which retains the crescent-shape of the terminal end. The terminal end 102 shape can also be described as C-shaped, semi-circular, arced, curved, etc.

The mesh body 103 begins as a strip, possibly a rectangular strip, and is formed through the methods described herein to have at least one, preferably two tapered end portions 104. The tapered end portions 104 meet the body 103 at intersections 105, though it is to be clear that the end portions 104 are a continuous extension of the mesh body 103 and are distinguished therefrom by the shaping methods described herein. It is also to be understood that the mesh construct of the mesh body 103 may differ from that of the tapered end portions. However, the taper created in the tapered end portions 104 results from the methods described herein and does not arise from removal of material from the elongate strip.

The third step of the inventive sling-forming method is the over-molding process in which the crescent-shaped end 102 of the mesh is affixed within the smaller diameter of a plastic anchor 200. Alternatively stated, the anchor 200 is formed over and incorporates the crescent-shaped end 102 of the mesh.

Figure 11:
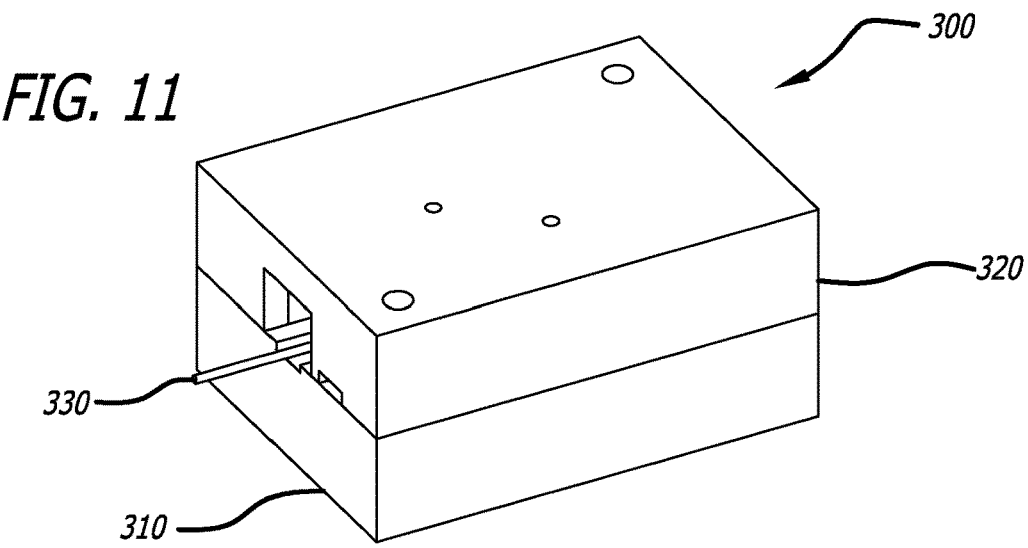
FIG. 11 is a transparent perspective view of an embodiment of a mold assembly of the invention.

Referring now to FIG. 11, the over-molding process involves a mold assembly 300 which generally includes three parts, the upper half 320, the lower half 310 and the core pin 330. FIG. 11 shows the mold assembly comprising the upper half 320, lower half 310 and core pin 330, in an assembled state.

Figure 12:
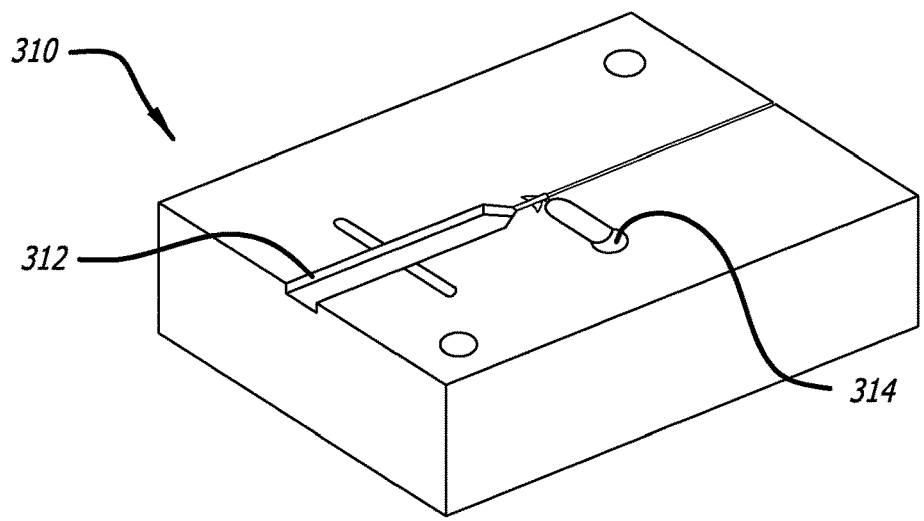
FIG. 12 is a perspective view of an embodiment of a lower half of a mold assembly of the invention.
Figure 13:
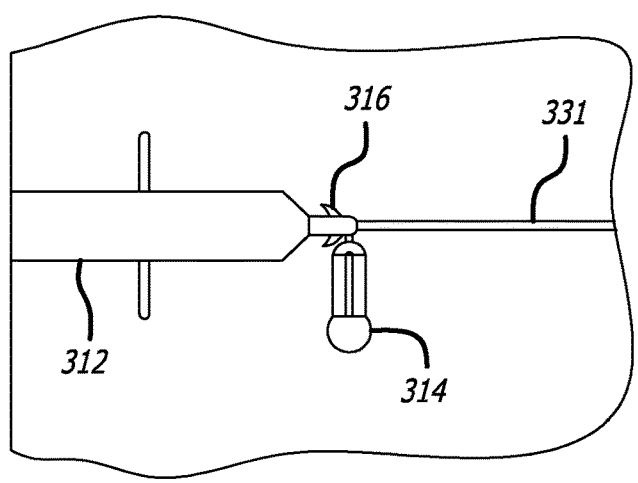
FIG. 13 is a partial plan view of an embodiment of a lower half of a mold assembly of the invention.

FIGS. 12 and 13 demonstrate different views of the lower half 310 of the mold assembly employing a mesh placement cavity 312 in which the sling 100 with the crescent-shaped terminal end 102 is placed; a core pin channel 331; and a material injection gate 314 through which plastic to form the anchors flows into an anchor mold portion 316 of the mold assembly.

Figure 14:
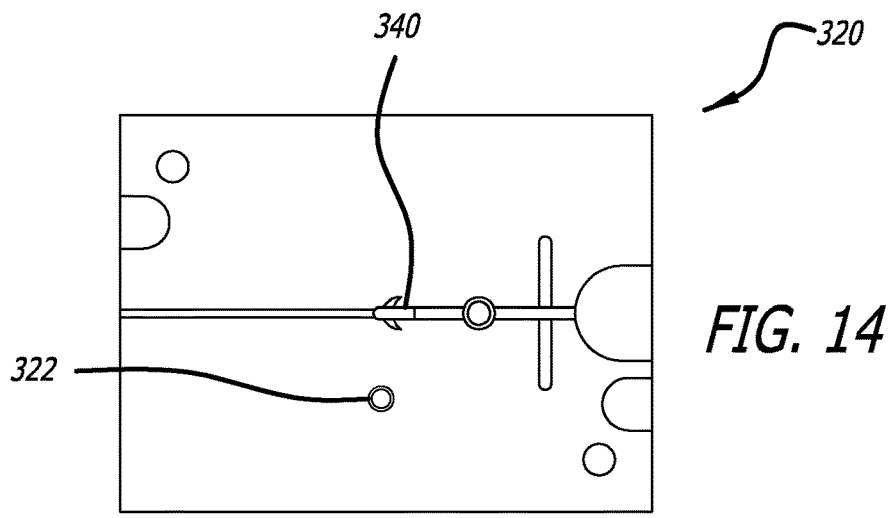
FIG. 14 is a bottom plan view of an embodiment of an upper half of a mold assembly of the invention.
Figure 15:
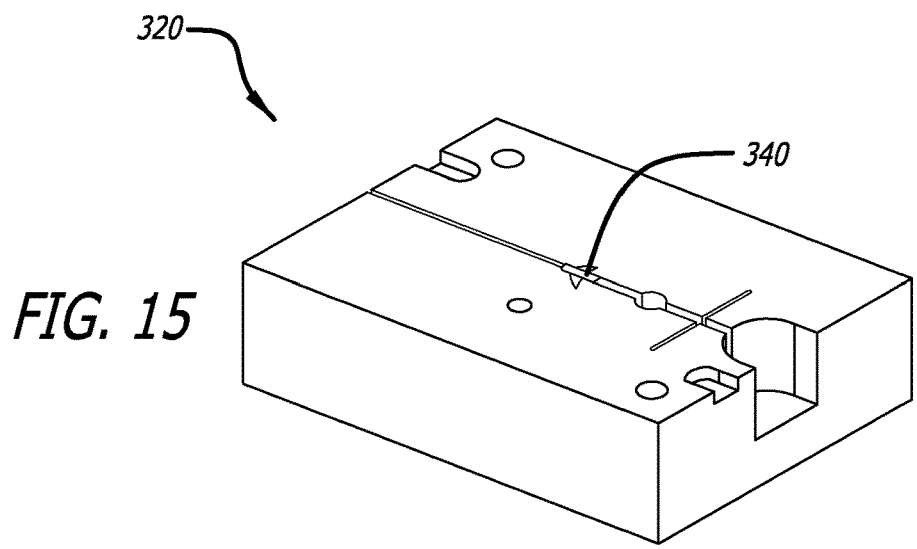
FIG. 15 is a perspective view of an embodiment of an upper half of a mold assembly of the invention.

FIGS. 14 and 15 demonstrate different views of the upper half 320 of the mold assembly employing a channel 322 through which plastic flows to gate 314 to form the anchor. The upper half includes an upper mold portion 340, which complements the anchor mold portion 316 of the lower half 310 in order to form a complete anchor. The details of the anchor are discussed below. The upper half 320 also includes a core pin channel 341, which complements the core pin channel 331 of the lower half 310.

Figure 16:
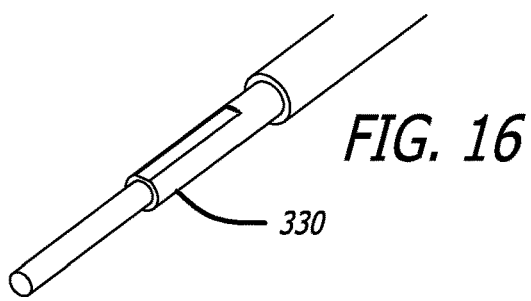
FIG. 16 is a perspective view of an embodiment of a core pin of the invention.
Figure 17:
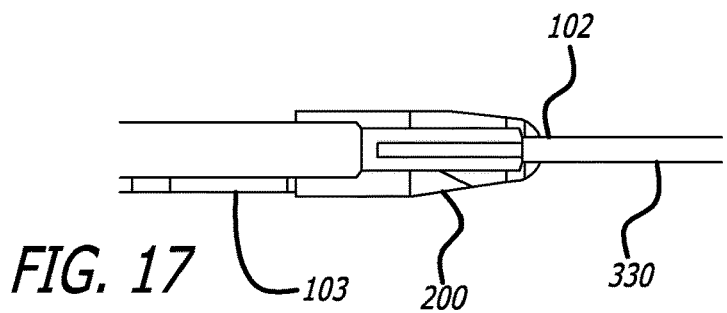
FIG. 17 is an elevation of an embodiment of an anchor of the invention with a core pin.

FIG. 16 shows the core pin 330 of the mold assembly 300. FIG. 17 shows a partial cross-sectional view of the core pin 330 positioned through the anchor 200 formed over the mesh with crescent-shaped terminal end 102, e.g. after formation of the anchor 200 over the mesh with the crescent-shaped terminal end 102 and removal of the sling 100 and core pin 330 from the mold assembly 300.

During formation of anchor 200 on the sling 100, the crescent-shaped terminal end 102 of the mesh is first situated within the mesh placement cavity 312 in the lower half 310 of the mold assembly and the core pin 330 is placed into the core pin channel 331. The upper half 320 of the mold assembly is secured to the lower half 310 and molten plastic is introduced through channel 322 and gate 314 and into anchor mold portion 316. The assembly is allowed to cool so as to solidify the formed anchor 200, the sling 100 is removed from the assembly 300, and the gate is cut from the anchor 200.

The gate 314 and the anchor mold portion 316 are designed to allow sufficient plastic material flow around the crescent-shaped terminal end 102 and the core pin 330 while minimizing the size of the anchor 200. After removal of the sling 100 from the assembly 300, the core pin 330 is withdrawn from the anchor 200 thereby leaving a cavity 210 formed through the anchor 200 for receipt of a distal end of a surgical tool for placement of the anchor within a patient. In certain embodiments, the exterior shape of the core pin 330 has features, e.g. asymmetric features and/or surfaces, that allow the anchor to be securely connected to the tool and prevent rotation or accidental disengagement.

Figure 18:
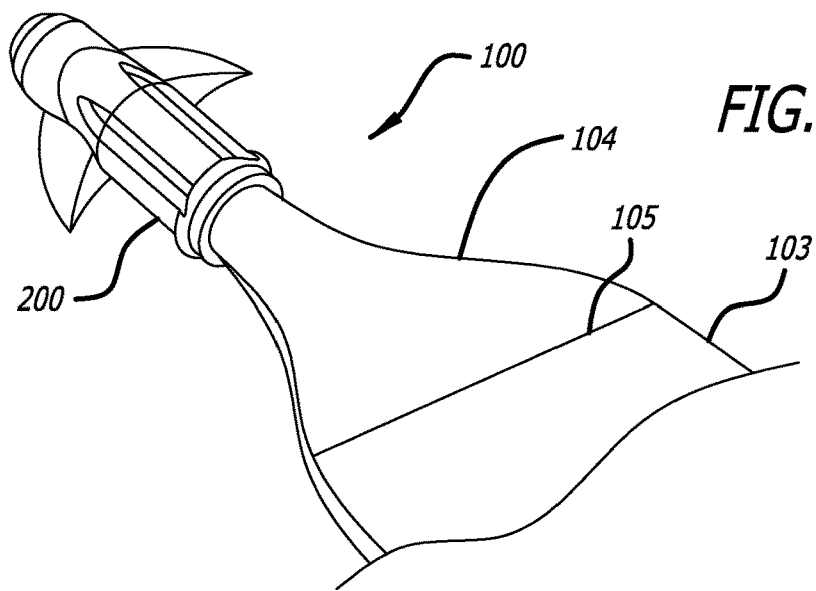
FIG. 18 is a perspective view of an embodiment of an anchor of the invention.
Figure 19:
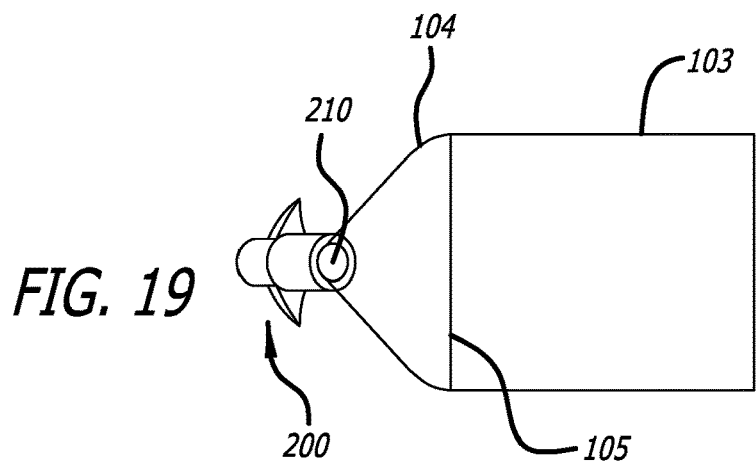
FIG. 19 is a perspective view of an embodiment of an anchor of the invention.
Figure 20:
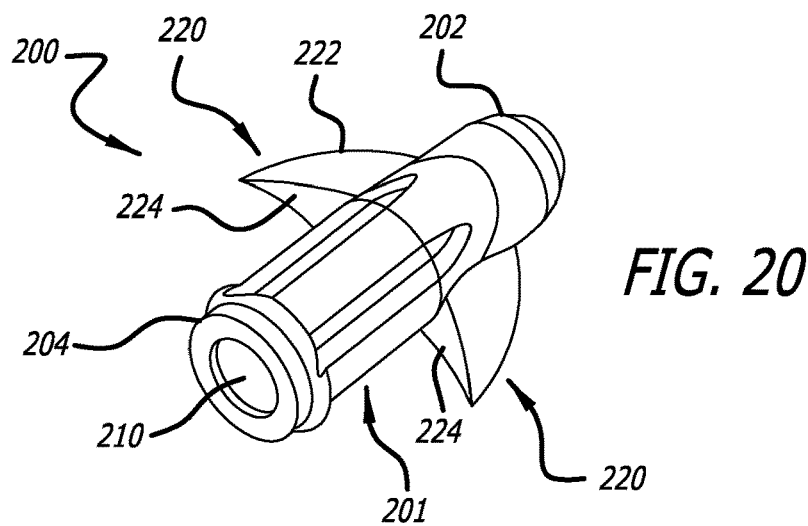
FIG. 20 is a perspective view of an embodiment of an anchor of the invention.

FIG. 18 demonstrates a terminal end or terminus 102 of the sling 100 over-molded with the anchor 200 as described above. FIG. 19 shows an inside view of the cavity 210 of the anchor 200 which results from the placement of the core pin 330 inside the channel 331 during formation of the anchor and from which the core pin 330 is taken out after formation of the anchor.

FIGS. 20-26 show the anchor 200. The anchor 200 has a body 201 with a proximal end 204 and a distal end 202 and the cavity 210. Tissue-grabbing features 220 extend from the body 201, and are shown as being embodied by two wings 220 placed on opposite sides of the body 201. The tissue grabbing features 220 may be alternatively embodied as a single feature or a plurality of features. Additionally, instead of being shaped like wings, non-limiting examples of these features include a ridge or ridges extending partially or completely around the body, barbs, hooks, spikes, posts, fins, textured surfaces, adhesives, in-growth promoting surfaces, etc.

The embodiment of the wings 220 shown in the figures include a leading edge 222, a trailing edge 224 and a lateral edge 226. The leading edge sweeps from the body 201 proximally back to the trailing edge 224. The trailing edge 224 joins the leading edge 222 and the lateral edge 226. The lateral edge 226 joins the trailing edge 224 and the lateral edge 226.

The leading edge 222 is shown as tapering to a point or sharpened edge in order to aid in separating tissue as it is pushed therethrough. The leading edge 222 alternatively may be curved, flat, rounded, or comprise two concave surfaces joining together.

The trailing edge 224 results from a termination of the leading edge 222 and thus has the shape of a cross-section of the leading edge 222. The trailing edge 224 is shown as being swept proximally such that it extends further in a proximal direction than the lateral edge 226, which is shown as extending relatively perpendicularly to the body 201.

Figure 21:
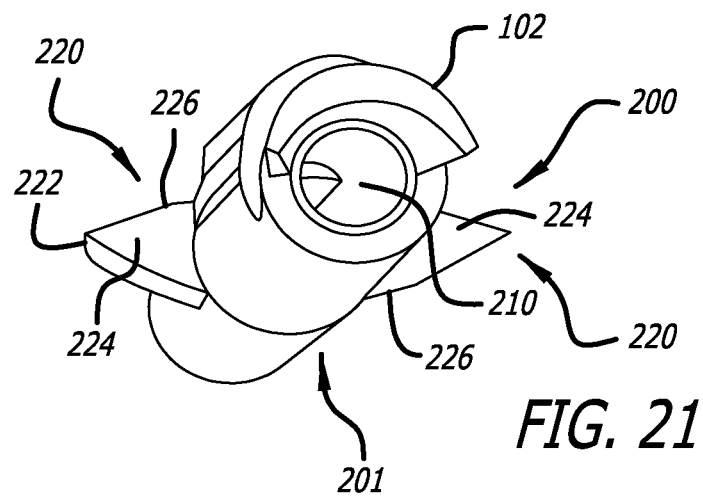
FIG. 21 is a perspective view of an embodiment of an anchor of the invention.
Figure 22:
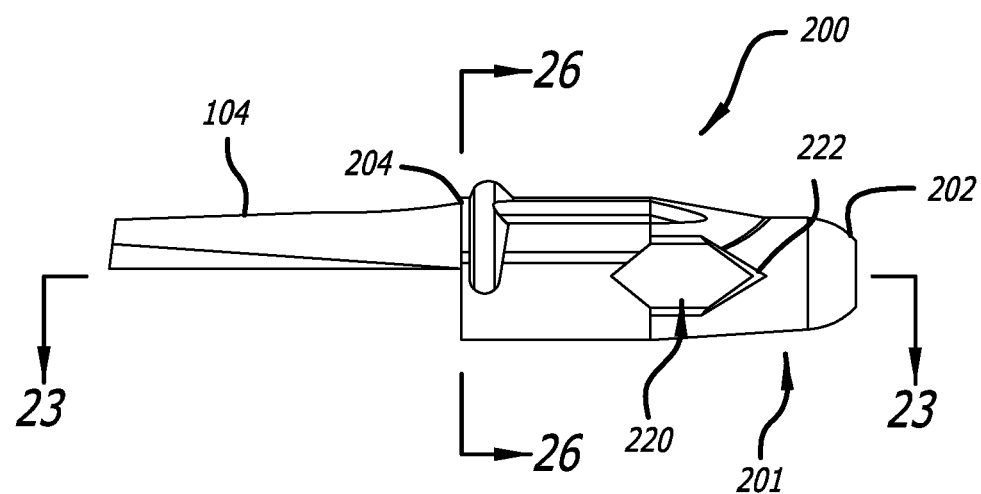
FIG. 22 is a side elevation of an embodiment of an anchor of the invention.
Figure 25:
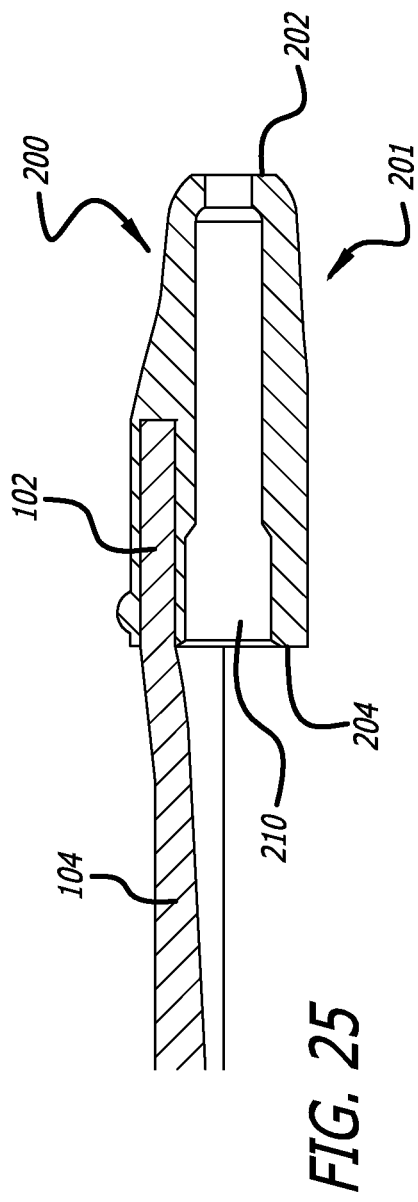
FIG. 25 is a section view of the embodiment of the anchor of FIG. 24 taken along section lines F-F.
Figure 26:
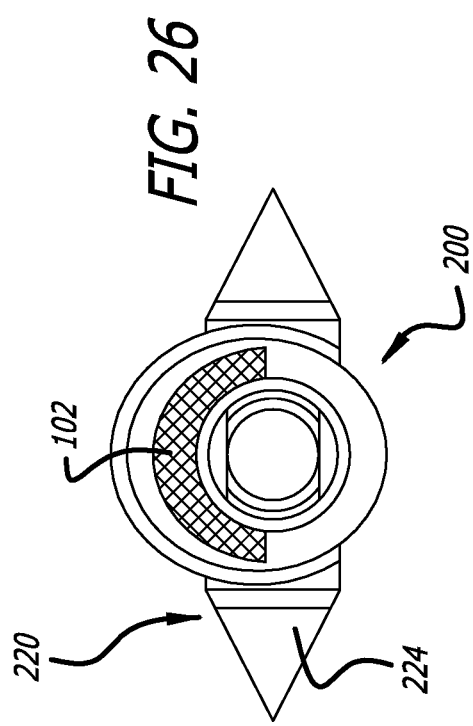
FIG. 26 is a section view of the embodiment of the anchor of FIG. 22 taken along section lines E-E.
Figure 27:
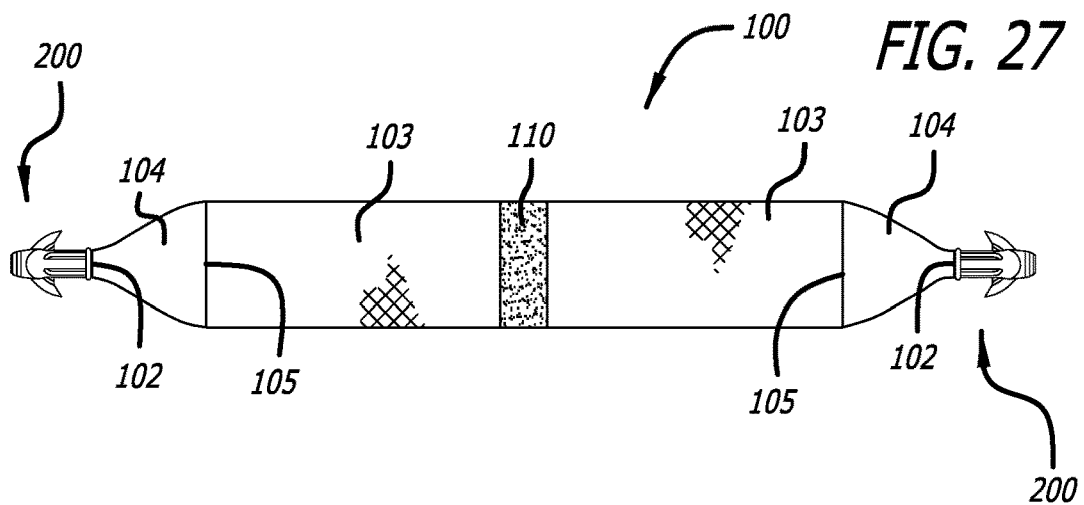
FIG. 27 is a plan view of an embodiment of a sling of the invention.
Figure 28:
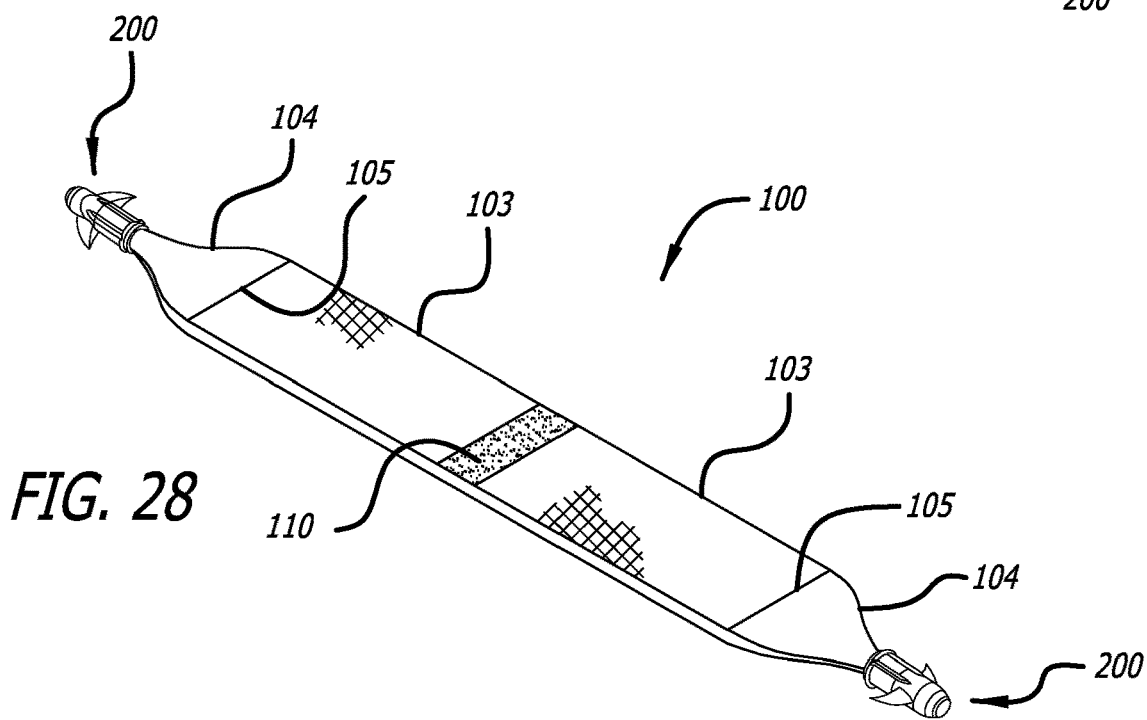
FIG. 28 is a perspective view of an embodiment of a sling of the invention.
Figure 29:
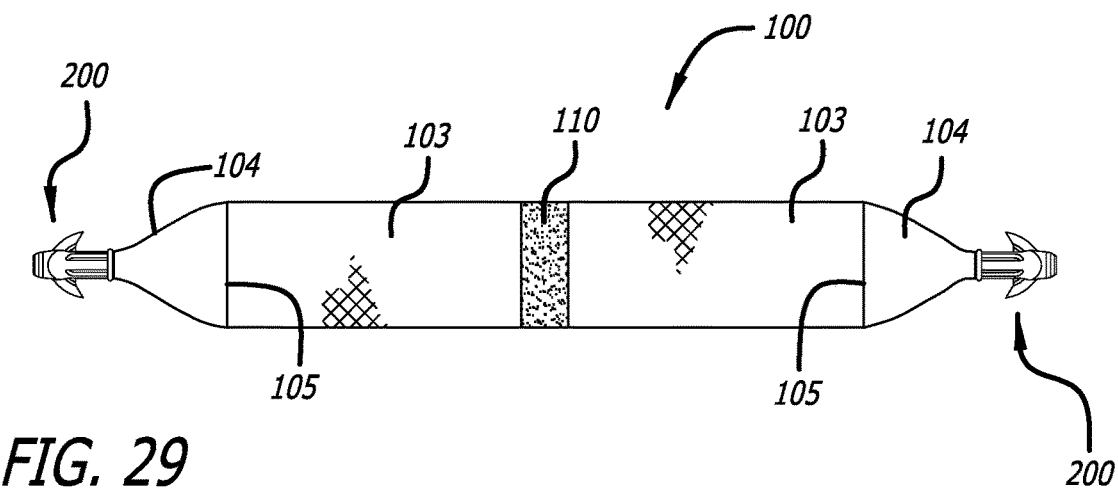
FIG. 29 is a plan view of an embodiment of a sling of the invention.
Figure 30:
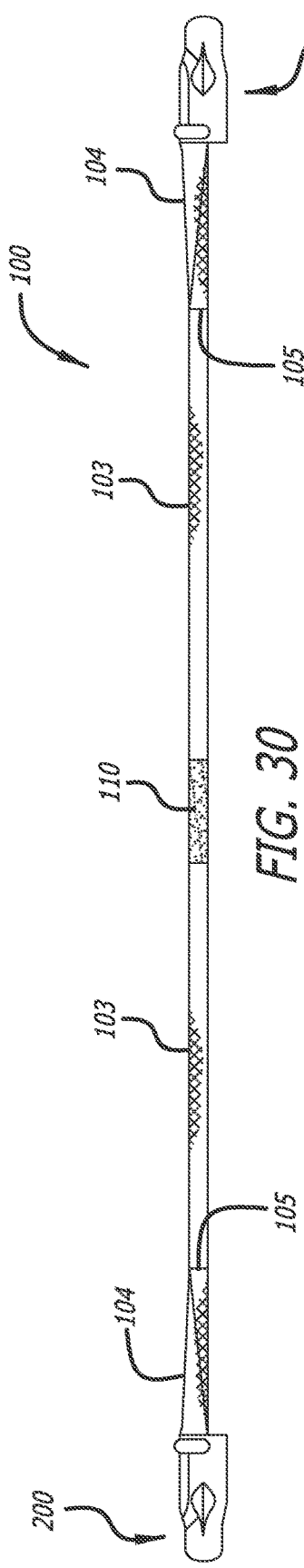
FIG. 30 is a side elevation of an embodiment of a sling of the invention.

FIG. 21 is a view of the proximal end 204 of the anchor 200 with a portion of C-shaped terminal end 102 of the mesh extending therefrom.

FIGS. 27-30 show an assembled single incision sling 100 with two anchors 200 secured at the terminal ends 102 through an over-molding process. A radiopaque band 110 may be included to provide a centering reference to assist in installation. The radiopaque band may be of a radiopaque mesh material or may be a radiopaque coating applied over the mesh body 103.

In some embodiments, the present invention discloses a single incision sling wherein the terminal ends of the sling with larger widths are each affixed within a smaller width of the plastic anchor without compromising the strength of the sling. In some embodiments, the widths of the proximal and the distal ends of the sling mesh are about 11 mm and are secured inside the anchors at both ends where the anchors have diameters of about 2 mm. In certain embodiments, the present invention discloses a method of securing both ends of the sling within the plastic anchors to form the single incision sling. In some embodiments, this process involves thermosetting the sling end and over-molding the sling end to secure it inside the anchor.

Figure 31:
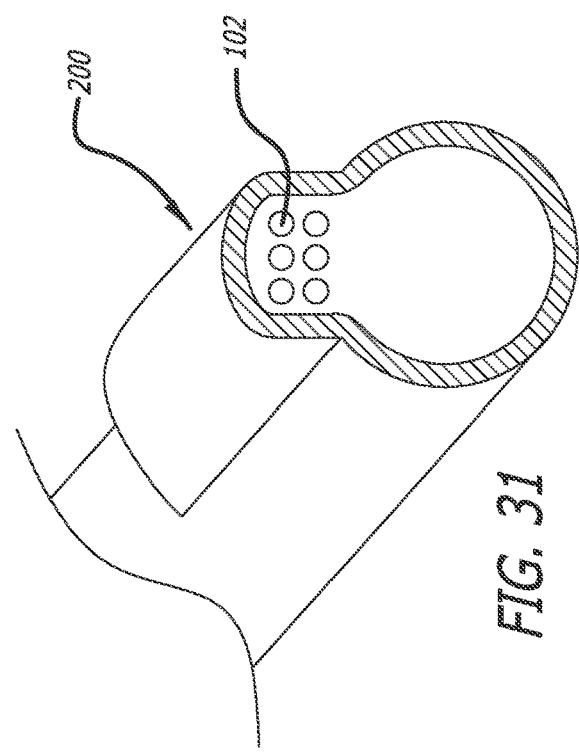
FIG. 31 is a partial perspective view of an embodiment of an anchor of the invention.

FIGS. 31-36 show various methods for attaching the mesh sling 100 to the anchors. FIG. 31 shows the sling 100 attached to the anchor 200 via over-molding, as described above.

Figure 32:
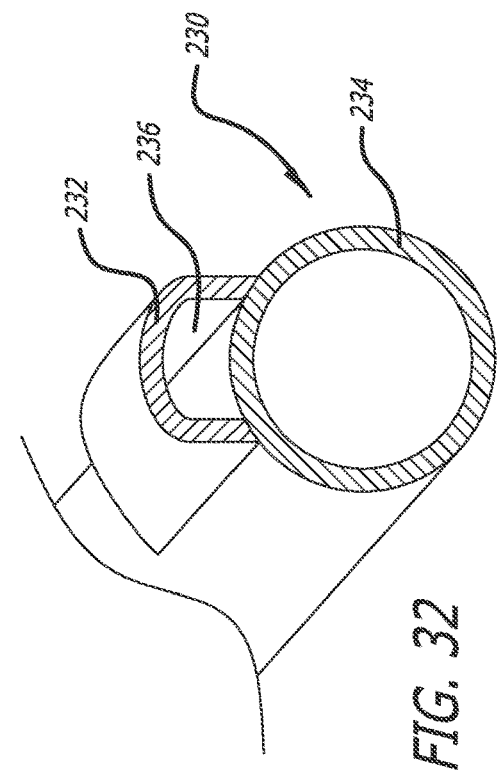
FIG. 32 is a partial perspective view of an embodiment of an anchor of the invention.

FIG. 32 shows a similar form of over-molding but includes an anchor 230 being molded to create a body 234 having a bridge 232 extending therefrom that defines a cavity 236 into which the sling is over-molded.

Figure 33:
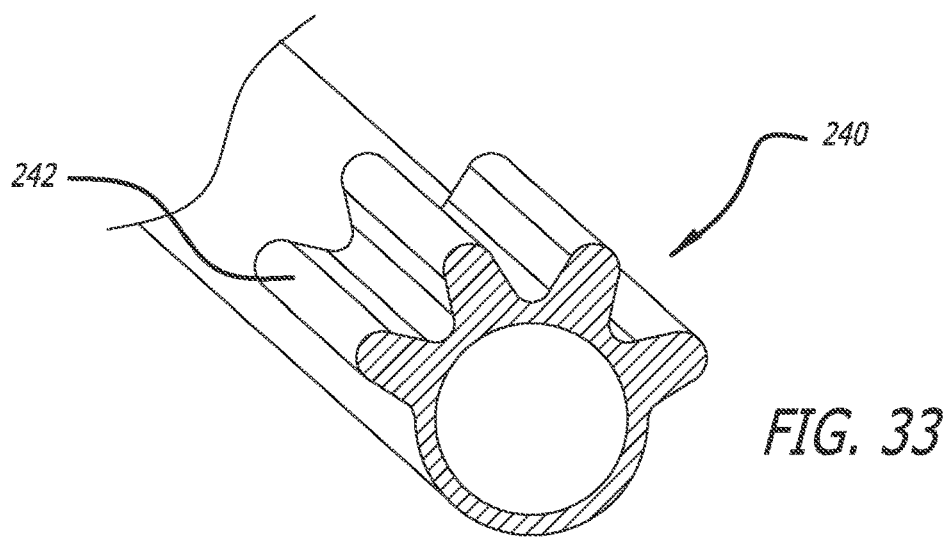
FIG. 33 is a partial perspective view of an embodiment of an anchor of the invention.

FIG. 33 shows an anchor 240 having surface features 242 in the form of bumps to increase the surface area available for adhesion. The sling mesh terminus may then be molded onto the features 242 or otherwise adhered to them.

Figure 34:
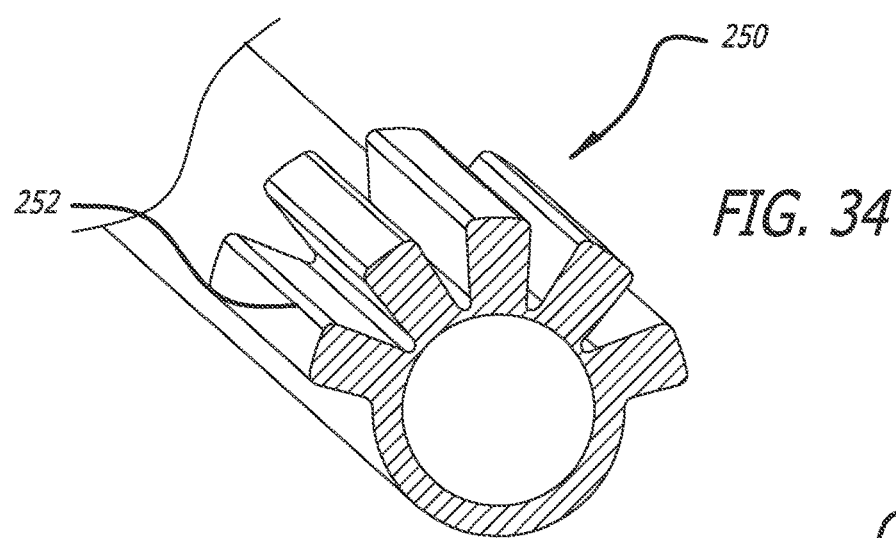
FIG. 34 is a partial perspective view of an embodiment of an anchor of the invention.

FIG. 34 provides an anchor 250 having grooves 252 into which a terminus 102 may be pressed in order to attach the mesh to the anchor.

Figure 35:
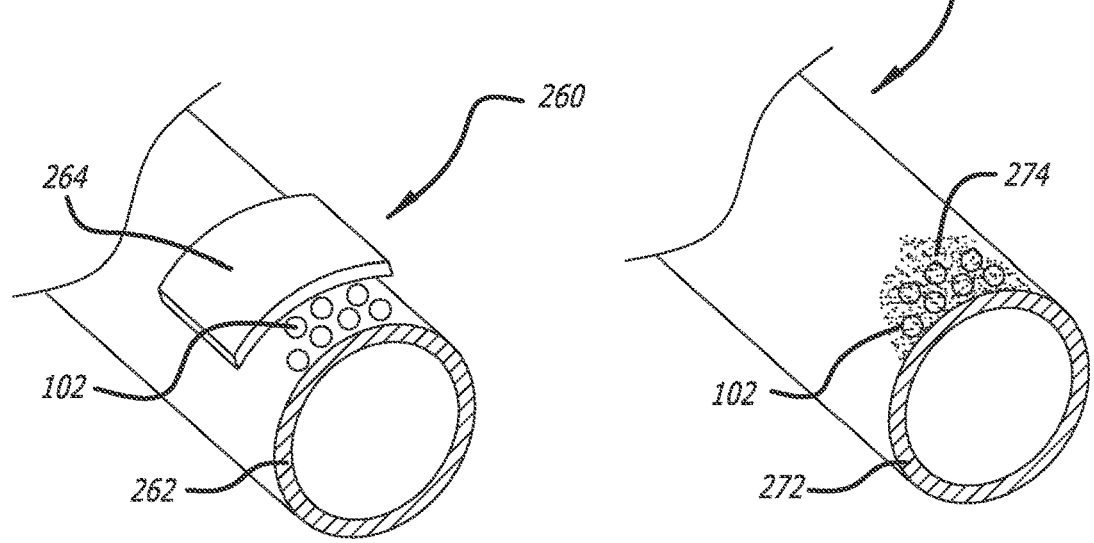
FIG. 35 is a partial perspective view of an embodiment of an anchor of the invention.

FIG. 35 shows an anchor 260 including a body 262. The mesh terminus 102 is attached to the body with a separate piece of material 264 which is then thermally joined to the body 262.

Figure 36:
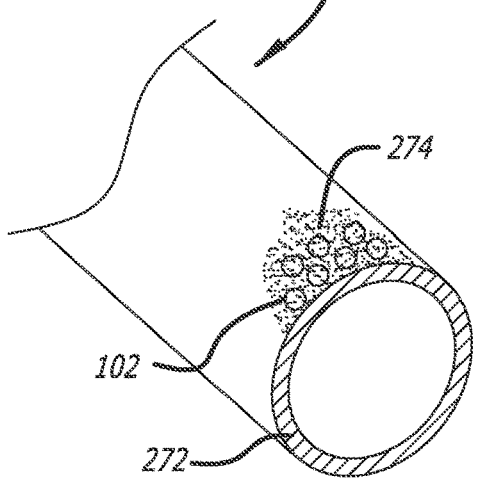
FIG. 36 is a partial perspective view of an embodiment of an anchor of the invention.

FIG. 36 shows a tubular anchor 270 with a terminus 102 attached to the body 272 with epoxy 274.

Figure 39:
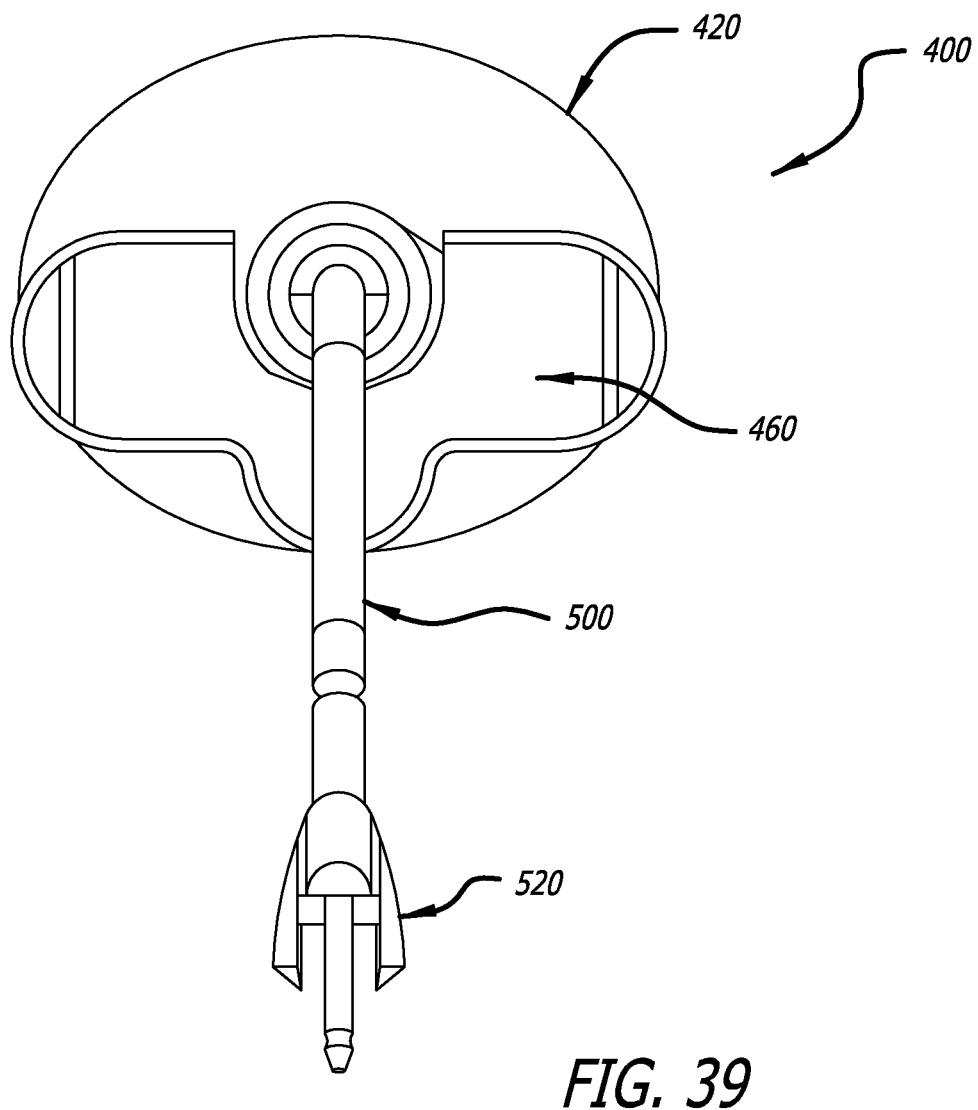
FIG. 39 is a front elevation of an embodiment of an introducer of the invention.

Turning now to FIGS. 37-47, an introducer 400 for use with the sling 100 is described. FIGS. 37-39 show a top plan view, a side elevation, and a front elevation, respectively, of the introducer 400, which includes a handle 420, a release mechanism 460 partially contained within the handle 420, a shaft 500 and an end piece 520.

Figure 40:
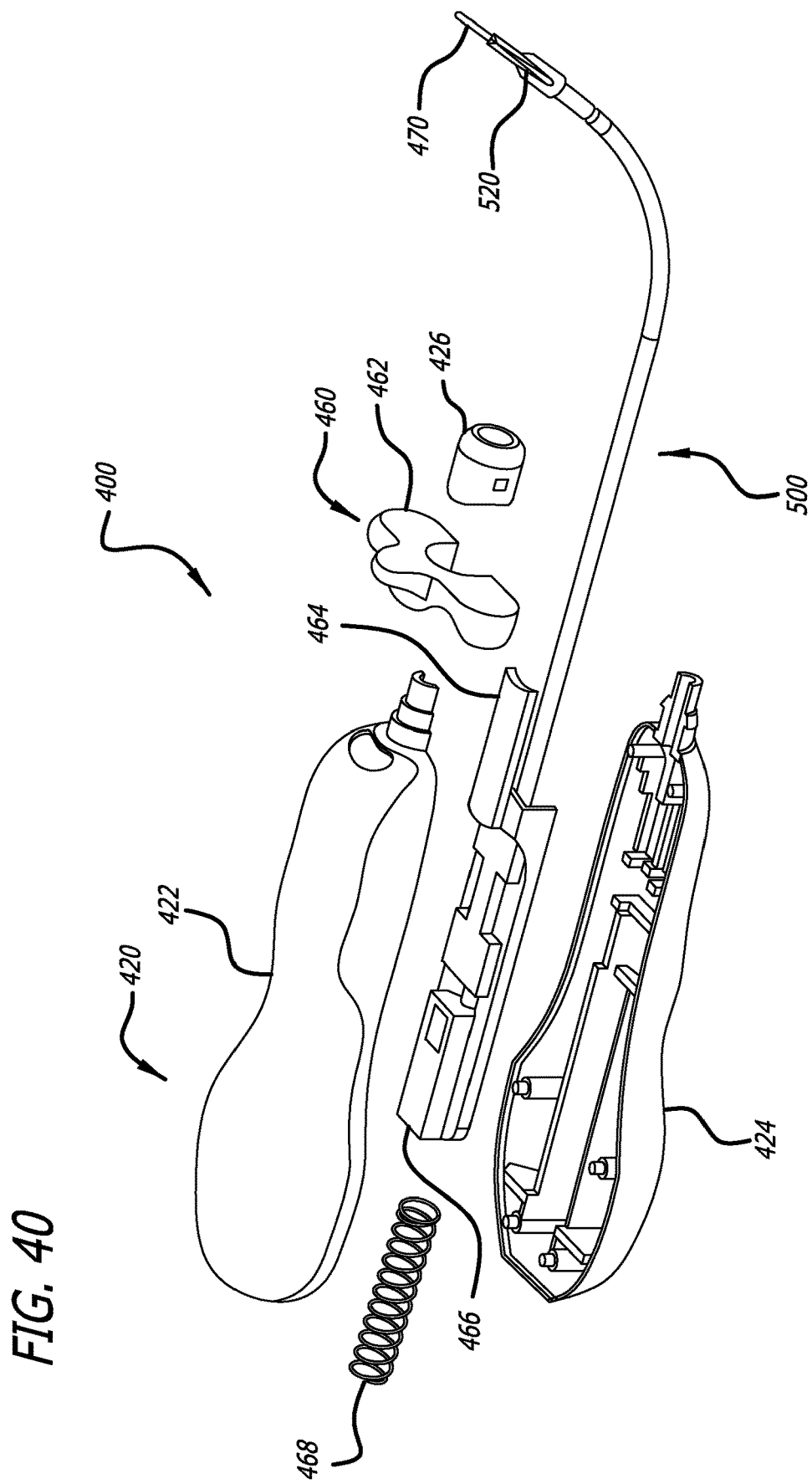
FIG. 40 is an exploded view of an embodiment of an introducer of the invention.

FIG. 40 shows the introducer 400 in an exploded view. The handle 420 includes a top half 422 and a bottom half 424 and includes a plurality of internal molded features designed to keep the internal components of the release mechanism 460 in place. An end cap 426 fits over the matching distal ends of the top half 422 and bottom half 424 and aids in joining the top half 422 and bottom half 424.

The release mechanism 460 includes an actuator 462 that is ergonomically shaped for activation by a user. The actuator 462 is either attached to, or integral with, an extension 464, which links the actuator 462 to an internal slide block 466. The extension 464 is integral with the slide block 466.

The slide block 466 interacts with the internal features of the top and bottom halves 422 and 424 of the handle 420 and is limited thereby to fore and aft movements. The slide block acts against a spring 468, contained by the handle at a proximal end and biases the slide block distally. At a distal end, the slide block is connected to an engagement pin 470, which is slideably contained within a lumen of the shaft 500. The engagement pin 470 is shaped to fit within the lumen 210 of the anchor 200 and preferably includes at least one non-cylindrical feature that prevents the anchor 200 from rotating around the pin 470 when the pin 470 and the anchor are engaged.

Figure 41:
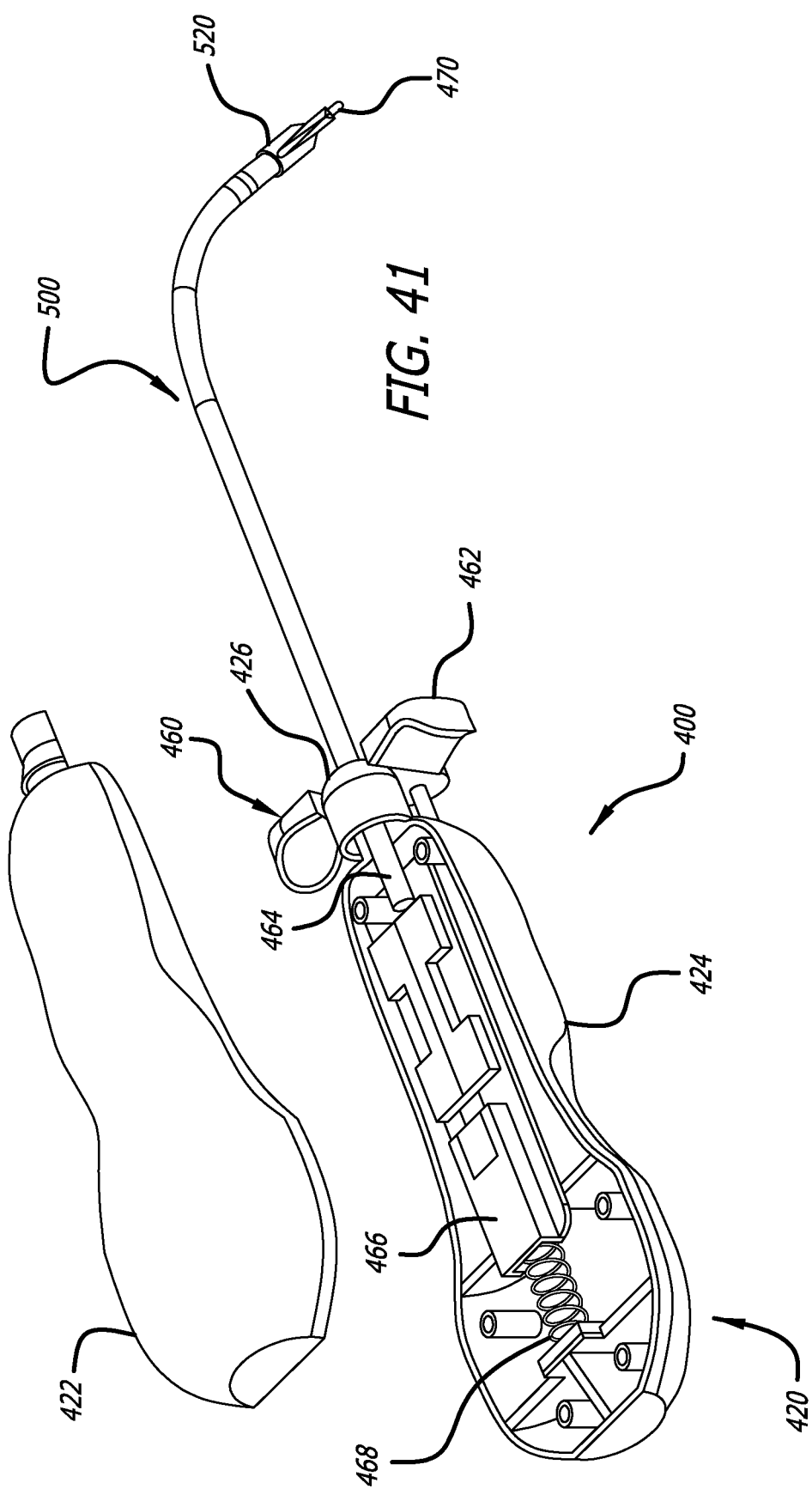
FIG. 41 is a perspective view of an embodiment of an introducer of the invention with a top half of the handle separated to show interior detail
Figure 46:
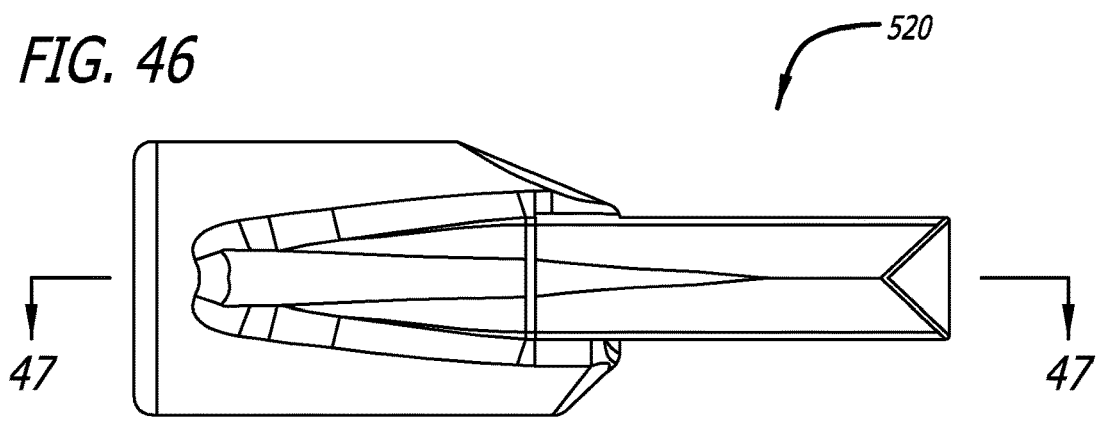
FIG. 46 is a side elevation of an embodiment of an end piece of the invention.
Figure 47:
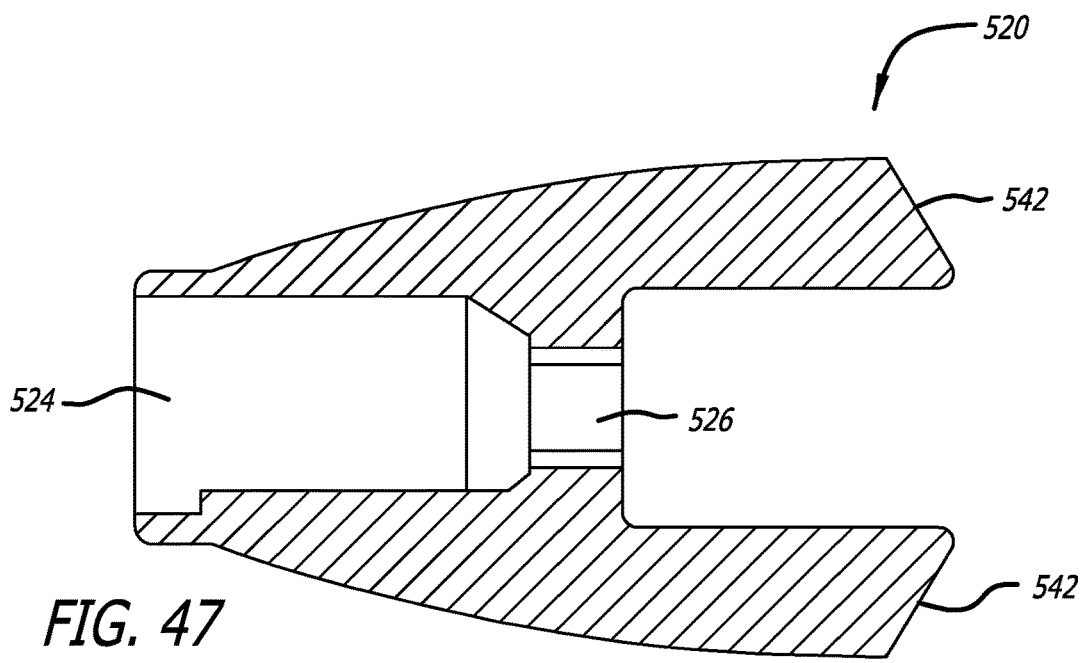
FIG. 47 is a sectional view of the embodiment of the end piece of FIG. 46 taken along lines A-A; and, FIG. 48 is a distal elevation of an embodiment of an end piece of the invention.
Figure 48:
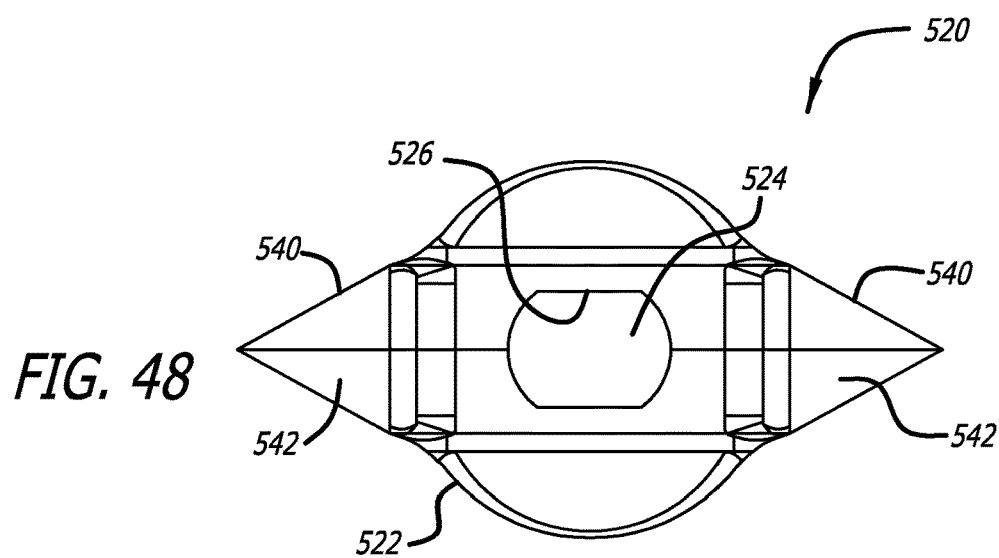

FIG. 41 shows the introducer 400 partially assembled with only the handle top half 422 removed. This perspective view shows the interaction between the release mechanism 460 and the internal features of the bottom half 424 of the handle 420.

FIGS. 42-48 depict various views of the end piece 520. The end piece 520 includes a body 522, a pair of disengagement wings 540 extending distally from the body and creating a U-shaped cavity between the distal end of the body and the inside surfaces of the disengagement wings 540. In one embodiment, the disengagement wings 540 are integral with the body 522. The body 522 defines a lumen 524, which includes surface features 526 that are configured to accept the engagement pin 470. The disengagement wings 540 include distal surfaces 542 that, in some embodiments, engage the trailing edges 224 of the anchor wings 220, and are shaped to match.

In other embodiments, when the anchor 200 is mated with the introducer 400, the trailing edges 224 of the anchor wings 220 are slightly separated from each other. The gap between the edges 224 and the anchor wings 220, allow tissue to catch the outside of the trailing edge 224 of the anchor wings and assist in the separation of the anchor from the introducer when actuated.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of forming a medical sling device comprising:
providing a rectangular strip of material having two end portions and an elongate body between the two end portions;
tapering at least one of said two end portions without removing said material therefrom by bunching said material in such a manner a terminus of said at least one end portion has a smaller width than an intersection between said at least one end portion and said elongate body, wherein bunching said material comprises pulling said rectangular strip through a fixture assembly having a tapered circular end comprising a wave-form opening;
thermosetting said at least one end portion such that said at least one end portion maintains said smaller width when unconstrained;
placing said at least one end portion in a mold;
forming an anchor around said terminus.

2. The method of claim 1 wherein said bunching said material results in a waveform.

3. The method of claim 1 wherein said fixture assembly comprises:
a fixture bottom having a groove with a wide end and a narrow end, the narrow end having a curved form with gaps on either side of said curved form;
a fixture top having a groove with a wide end and a narrow end, the narrow end having a center fin and a curved form on either side of the center fin;
wherein when said fixture top is placed on said fixture bottom and aligned therewith, said center fin points down toward said fixture bottom curved form, thereby creating a wave-like gap through which said rectangular strip may be pulled to create said smaller width in said at least one end portion.

4. The method of claim 3 wherein said fixture further comprises a shaping rod extending from said narrow end of said groove.

5. The method of claim 1 wherein thermosetting said at least one end portion such that said at least one end portion maintains said smaller width when unconstrained comprises:
pulling said rectangular strip through said fixture assembly to create a waveform;
pulling said waveform further and onto a shaping rod; and,
heat-shrinking tubing over said waveform to form said waveform into the shaping rod to create a crescent-shape.

6. The method of claim 5 further comprising removing said tubing prior to placing said at least one end portion in said mold.

7. A method of forming a medical sling device comprising:
providing a strip of material having two end portions and an elongate body between the two end portions;
tapering at least one of said two end portions without removing said material therefrom by creating a wave-like configuration in said material such that a terminus of said at least one end portion has a smaller width than an intersection between said at least one end portion and said elongate body, wherein tapering at least one of said two end portions without removing said material therefrom further comprises pulling said strip of material through a fixture assembly having a tapered circular end comprising a wave-form opening;
placing said at least one end portion in a mold;
forming an anchor around said terminus.

8. The method of claim 7 further comprising thermosetting said at least one end portion such that said wave-like configuration is maintained while placing said at least one end portion in said mold.

9. The method of claim 7 wherein said fixture assembly comprises:
a fixture bottom having a groove with a wide end and a narrow end, the narrow end having a curved form with gaps on either side of said curved form; and,
a fixture top having a groove with a wide end and a narrow end, the narrow end having a center fin and a curved form on either side of the center fin;

wherein when said fixture top is placed on said fixture bottom and aligned therewith, said center fin points down toward said fixture bottom curved form, thereby creating a wave-like gap through which said strip may be pulled to create said wave-like configuration in said at least one end portion.

10. A medical sling comprising:
an elongate strip of material having two ends and a support portion between said two ends, wherein said two ends and said support portion comprise a uniform cross-sectional material of said elongate strip;
wherein each of said two ends comprise thermoset portions having a crescent shape; and,
over-molded anchors positioned over said thermoset portions;
wherein each anchor comprises a cavity having asymmetric surfaces and said cavity expands between a proximal end and a distal end of each anchor.

11. The medical sling of claim 10 wherein said anchors each comprise:
a body;
tissue-grabbing features extending outwardly from said body.

12. The medical sling of claim 11 wherein said tissue grabbing features comprise at least one wing having a leading edge and a trailing edge and wherein the leading edge sweeps from said body back to said trailing edge.

13. The medical sling of claim 12 wherein said trailing edge extends forward from said leading edge to a lateral edge.

14. The medical sling of claim 13 wherein said lateral edge extends perpendicularly from said body to said trailing edge.

15. The medical sling of claim 10 wherein said elongate strip of material comprises a rectangular shape prior to said two ends being formed into said crescent shape.

16. The medical sling of claim 10 wherein said crescent shape creates a taper in said elongate strip near said two ends.

17. The medical sling of claim 10 wherein said anchors each further comprise said cavity useable to receive an implantation device.

18. The medical sling of claim 10 wherein said two ends are thermoset into said crescent shape that partially surrounds said cavity.

19. A method of forming a medical sling device comprising:
providing a rectangular strip of material having two end portions and an elongate body between the two end portions;
tapering at least one of said two end portions without removing said material therefrom by bunching said material in such a manner a terminus of said at least one end portion has a smaller width than an intersection between said at least one end portion and said elongate body;
wherein bunching said material comprises pulling said rectangular strip through a fixture assembly;
wherein said fixture assembly comprises:
a fixture bottom having a groove with a wide end and a narrow end, the narrow end having a curved form with gaps on either side of said curved form;
a fixture top having a groove with a wide end and a narrow end, the narrow end having a center fin and a curved form on either side of the center fin;
wherein when said fixture top is placed on said fixture bottom and aligned therewith, said center fin points down toward said fixture bottom curved form, thereby creating a wave-like gap through which said rectangular strip may be pulled to create said smaller width in said at least one end portion;
thermosetting said at least one end such that said at least one end maintains said smaller width when unconstrained;
placing said at least one end portion in a mold;
forming an anchor around said terminus.

20. The method of claim 19 wherein said fixture further comprises a shaping rod extending from said narrow end of said groove.

21. A method of forming a medical sling device comprising:
providing a rectangular strip of material having two end portions and an elongate body between the two end portions;
tapering at least one of said two end portions without removing said material therefrom by bunching said material in such a manner a terminus of said at least one end portion has a smaller width than an intersection between said at least one end portion and said elongate body;
wherein bunching said material comprises pulling said strip through a fixture assembly;
wherein said fixture assembly comprises:
a fixture bottom having a groove with a wide end and a narrow end, the narrow end having a curved form with gaps on either side of said curved form; and,
a fixture top having a groove with a wide end and a narrow end, the narrow end having a center fin and a curved form on either side of the center fin;
wherein when said fixture top is placed on said fixture bottom and aligned therewith, said center fin points down toward said fixture bottom curved form, thereby creating a wave-like gap through which said strip may be pulled to create said wave-like configuration in said at least one end portion.

* * * * *